United States Patent
Aarden et al.

(10) Patent No.: US 10,034,442 B2
(45) Date of Patent: Jul. 31, 2018

(54) TOMATO PLANTS WITH IMPROVED AGRONOMIC TRAITS

(71) Applicant: Seminis Vegetable Seeds, Inc., St. Louis, MO (US)

(72) Inventors: Harriette Aarden, St. Louis, MO (US); Ami Bar, Lehavot Habashan (IL); Bernardus van den Bosch, Zoetermeer (NL); Albert Grit, Ermelo (NL); Amit Hotzev, Nirit Settlement (IL); Arnon Osri, Rosh Hanikra (IL); Maria Fernanda Rodriguez, St. Louis, MO (US); Bram Rozier, St. Louis, MO (US); Alberto Vecchietti, St. Louis, MO (US); Ruth Wagner, St. Louis, MO (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 14/857,688

(22) Filed: Sep. 17, 2015

(65) Prior Publication Data

US 2016/0100538 A1    Apr. 14, 2016

Related U.S. Application Data

(60) Provisional application No. 62/052,320, filed on Sep. 18, 2014.

(51) Int. Cl.
    *A01H 5/08*      (2018.01)
    *A01H 5/00*      (2018.01)
    *C12Q 1/6895*    (2018.01)
    *C12N 15/00*     (2006.01)

(52) U.S. Cl.
    CPC ............ *A01H 5/08* (2013.01); *C12Q 1/6895* (2013.01); *C12Q 2600/13* (2013.01); *C12Q 2600/156* (2013.01)

(58) Field of Classification Search
    None
    See application file for complete search history.

(56) References Cited

U.S. PATENT DOCUMENTS

2005/0120418 A1*  6/2005  Fuerstenberg ........... A01H 1/04
                                                     800/287
2006/0064775 A1   3/2006  Frank et al.
2008/0313768 A1  12/2008  Heath
2011/0283402 A1  11/2011  Bunn et al.

FOREIGN PATENT DOCUMENTS

WO    WO 2001/049105    7/2001

OTHER PUBLICATIONS

Alseekh et al., "Resolution by recombination: breaking up *Solanum pennellii* introgressions," *Trends Plant Sci*, 18:536-538, 2013.

Arens et al., "Development and evaluation of robust molecular markers linked to disease resistance in tomato for distinctness, uniformity and stability testing," *Theor Appl Genet*, 120(3):655-664, 2010.
Baxter et al., "Fruit carbohydrate metabolism in an introgression line of tomato with increased fruit soluble solids," *Plant Cell Physiol*, 46:425-437 2005.
Eshed et al., An introgression line population of *Lycopersicon pennellii* in the cultivated tomato enables the identification and fine mapping of yield-associated QTL, *Genetics*, 141:1147-1162, 1995.
Eshed et al., "Less than additive epistatic interactions of quantitative trait loci in tomato," *Genetics*, 143:1807-1817, 1996.
Shi et al., "Molecular markers for Tm-2 alleles of tomato mosaic virus resistance in tomato," *Am J Pi Sci*, 2:180-189, 2011.
Sol Genomics Network. Available at https://solgenomics.net/. Retrieved Oct. 17, 2016.
The Tomato Genome Consortium, "The tomato genome sequence provides insights into fleshy fruit evolution," *Nature*, 485:635-641, 2012.
Zanor et al., "RNA Interference of LIN5 in Tomato Confirms Its Role in Controlling Brix Content, Uncovers the Influence of Sugars on the Levels of Fruit Hormones, and Demonstrates the Importance of Sucrose Cleavage for Normal Fruit Development and Fertility," *Plant Phys*, 150:1204-1218, 2009.
Friedman et al., Zooming in on a quantitative trait for tomato yield using interspecific introgressions, *Science*, 305(5691):1786-178, 2004.
Labate et al., "Evidence of cryptic introgression in tomato (*Solanum lycopersicum* L.) based on wild tomato species alleles," *BMC Plant Biology*, 12(3):1-12, 2012.
International Search Report and Written Opinion regarding International Application No. PCT/US 15/50757, dated Dec. 15, 2015.
European Extended Search Report regarding European Application No. EP 15841205, dated Jan. 19, 2018.
Alseekh et al., "resolution by recombination: breaking up *Solanum pennellii* introgressions," Trends in Plant Science 18:536-538, 2013.
Causse et al., "A genetic map of candidate genes and QTLs involved in tomato fruit size and composition," *Journal of Experimental Botany* 55:1671-1685, 2004.
Eshed et al., "Introgressions from *Lycopersicon pennellii* can improve the soluble-solids yield of tomato hybrids," *Theor. Appl. Genet.* 88:891-897, 1994.
Ikeda et al., "Analysis of a tomato introgression line, IL8-3, with increased Brix content," *Scientia Horticulturae* 153:103-108, 2013.
Vakalounakis, "The genetic analysis of resistance to fusarium crown and root rot of tomato," *Plant Pathology* 37:71-73, 1988.

* cited by examiner

*Primary Examiner* — Phoenix Bui
(74) *Attorney, Agent, or Firm* — Dentons US LLP; Matthew Madsen, Esq.

(57) ABSTRACT

The present disclosure provides tomato plants exhibiting improved fruit quality and disease resistance. Such plants may comprise novel introgressed genomic regions associated with improved fruit quality or disease resistance. In certain aspects, compositions, including novel polymorphic markers and methods for producing, breeding, identifying, and selecting plants or germplasm with an improved fruit quality or disease resistance phenotype are provided.

23 Claims, 8 Drawing Sheets

| Line No. | Pedigree | Pathology Score | Marker Designation ||||||||||||||
|---|---|---|---|---|---|---|---|---|---|---|---|---|---|---|---|---|
| | | | NSLYC0092375570 | NSLYC0092407700 | NL0216198 | NSLYC0084337311 | NSLYC0084337571 | NSLYC0084337690 | NSLYC0084337777 | NSLYC0084337961 | NSLYC0084338011 | NSLYC0084338021 | NSLYC0084338071 | NSLYC0084338341 | NSLYC0084338631 | NSLYC0084339311 | NL0241464 |
| 5027 | 11KY1100 | R | PER | PER | LYC | PER | PER | PER | LYC | – | PER | – | PER | PER | – | – | PER |
| 5028 | 11KY1105 | R | PER | PER | LYC | PER | PER | PER | LYC | – | PER | – | PER | PER | – | – | PER |
| 6192 | 04EA0512 | R | PER | PER | PER | PER | PER | PER | PER | PER | PER | PER | PER | PER | PER | PER | PER |
| 6384 | 12GD1080 | R | PER | PER | PER | PER | PER | PER | PER | PER | PER | PER | PER | PER | PER | PER | PER |
| 6616 | 12HF0005 | R | PER | PER | PER | PER | PER | PER | PER | PER | PER | PER | PER | PER | PER | PER | PER |
| 6686 | 12GS1002 | R | PER | PER | PER | PER | PER | PER | PER | PER | PER | PER | PER | PER | PER | PER | PER |
| 6711 | 12SM0002 | R | PER | PER | PER | PER | PER | PER | PER | PER | PER | PER | PER | PER | PER | PER | PER |
| 5113 | 12ES1001 | S | LYC | LYC | LYC | LYC | LYC | LYC | LYC | LYC | LYC | LYC | LYC | LYC | LYC | LYC | LYC |
| 6713 | 12SM0003 | S | LYC | LYC | LYC | LYC | LYC | LYC | LYC | LYC | LYC | LYC | LYC | PER | LYC | LYC | LYC |
| 6736 | 09SM0090 | S | LYC | LYC | LYC | LYC | LYC | LYC | LYC | LYC | LYC | LYC | LYC | LYC | LYC | LYC | LYC |
| 6760 | 12SM0006 | S | LYC | LYC | LYC | LYC | LYC | LYC | LYC | LYC | LYC | LYC | LYC | LYC | LYC | LYC | LYC |
| 5618 | 12EB1042 | S | LYC | LYC | LYC | LYC | LYC | LYC | LYC | LYC | LYC | LYC | LYC | LYC | PER | PER | PER |
| 5670 | 12EE1023 | S | LYC | LYC | LYC | LYC | LYC | LYC | LYC | LYC | LYC | LYC | LYC | LYC | PER | PER | PER |
| 6717 | 12SM0032 | S | LYC | LYC | LYC | LYC | LYC | LYC | LYC | LYC | LYC | LYC | LYC | LYC | PER | PER | PER |
| 5410 | 12ER0082 | R | LYC | LYC | LYC | LYC | LYC | LYC | LYC | – | PER | – | PER | PER | – | – | PER |
| 5411 | 12ER0083 | R | LYC | LYC | LYC | LYC | LYC | LYC | LYC | – | PER | – | PER | PER | – | – | PER |
| 5966 | 12EF1030 | R | LYC | LYC | LYC | LYC | LYC | LYC | LYC | – | PER | – | PER | PER | – | – | PER |
| 5968 | 12EF1032 | R | LYC | LYC | LYC | LYC | LYC | LYC | LYC | – | PER | – | PER | PER | – | – | PER |
| 5969 | 12EF1033 | R | LYC | LYC | LYC | LYC | LYC | LYC | LYC | – | PER | – | PER | PER | – | – | PER |
| 6250 | 12GP1054 | R | LYC | LYC | LYC | LYC | LYC | LYC | LYC | – | PER | – | PER | PER | – | – | PER |
| 6268 | 12GP1069 | R | LYC | LYC | LYC | LYC | LYC | LYC | LYC | – | PER | – | PER | PER | – | – | PER |
| 6617 | 12HF0009 | R | LYC | LYC | LYC | LYC | LYC | LYC | LYC | – | PER | – | PER | PER | – | – | PER |
| 5111 | 12EY1000 | S | LYC | LYC | LYC | LYC | LYC | LYC | LYC | LYC | LYC | LYC | LYC | LYC | LYC | LYC | LYC |
| 5199 | 12ES1012 | S | LYC | LYC | LYC | LYC | LYC | LYC | LYC | LYC | LYC | LYC | LYC | LYC | LYC | LYC | LYC |

| Inv BID | Sow code | geno | Q-NL0217199 | NSLYC009229170 | Q-NL0213564 | Q-NL0247854 |
|---|---|---|---|---|---|---|
| IXC00000007822759373045477 | 13TJD0300 | null | ESC | ESC | ESC | ESC |
| IXC00000007822759373173505 | 13TJD0301 | rec_hom | ESC | PEN | PEN | PEN |
| IXC00000007822759373042433 | 13TJD0302 | rec_het | ESC | HET | HET | HET |
| IXC00000007822759380091009 | 13TJD0303 | control | PEN | PEN | PEN | PEN |

FIG. 6

TOMATO PLANTS WITH IMPROVED AGRONOMIC TRAITS

CROSS REFERENCE TO RELATED APPLICATIONS

This application claims priority to U.S. Provisional Application No. 62/052,320, filed Sep. 18, 2014, which is herein incorporated by reference in its entirety.

FIELD OF THE INVENTION

The present invention relates to the field of crop science and more specifically to methods and compositions for producing tomato plants exhibiting improved fruit quality or disease tolerance.

INCORPORATION OF SEQUENCE LISTING

The sequence listing that is contained in the file named "SEMB017US_ST25.txt", which is 6,804 bytes as measured in Microsoft Windows operating system and was created on Sep. 17, 2015, is filed electronically herewith and incorporated herein by reference.

BACKGROUND OF THE INVENTION

Fruit quality and taste are important traits in the production of food crops. The taste of ripe tomato fruit is predominantly determined by sugar and titratable acid content, jointly measured in degrees Brix. Brix level is determined by environmental and genetic factors. Although alleles that increase Brix levels in tomato fruit have been identified in non-cultivated plant lines, efforts to introduce these alleles into cultivated lines have been hindered horticultural deficiencies. With any trait introgression from a wild relative, it is unknown whether the often found horticultural deficiencies are the result of pleiotropy, or due to by linkage drag. Linkage drag results from tightly associated genes near the gene of interest. Overcoming linkage drag is difficult, and a common hurdle to overcome is a lack recombination that would facilitate the separation of the genes causing drag, from the beneficial locus. Commonly, recombination can be suppressed in genomic regions introgressed from non-cultivated, wild relative species of a crop plant. The use of marker-assisted selection (MAS) in plant breeding methods has made it possible to select plants based on genetic markers linked to traits of interest. However accurate markers for identifying or tracking desirable traits in plants are frequently unavailable even if a gene associated with the trait has been characterized. These difficulties are further complicated by factors such as epistasis and polygenic or quantitative inheritance, which often lead to an incomplete understanding of the genetic background underlying expression of a desired phenotype. Therefore, in the absence of accurate and validated markers for use in MAS, it may not be feasible to produce new plant lines exhibiting certain beneficial phenotypes.

SUMMARY OF THE INVENTION

In one aspect, the invention provides a *Solanum lycopersicum* plant comprising a Lin5 allele from *Solanum pennellii*, a Fr1 allele from *Solanum peruvianum*, and a Tm2a allele from *S. peruvianum*, wherein said plant exhibits improved resistance to *Fusarium* crown and root rot and tomato mosaic virus, and elevated Brix levels relative to a plant lacking the Lin5, Fr1, and Tm2a alleles. In certain embodiments, the plant is homozygous for said Lin5 allele from *Solanum pennellii*, or the plant is homozygous for said Fr1 allele from *Solanum peruvianum*, or the plant is homozygous for said Tm2a allele from *S. peruvianum*. In another embodiment, the plant that is homozygous for said Tm2a allele from *S. peruvianum* exhibits decreased necrosis compared with a plant that is heterozygous for said Tm2a allele from *S. peruvianum*. In another embodiment, the plant is heterozygous for said Lin5 allele from *Solanum pennellii*, or the plant is heterozygous for said Fr1 allele from *Solanum peruvianum*, or the plant is heterozygous for said Tm2a allele from *S. peruvianum*. In other embodiments, a plant of the invention is inbred or is hybrid. In another embodiment, the invention provides a plant part of a plant in accordance with the invention. In a further embodiment, the plant part is a leaf, root, flower, fruit, pollen, ovule, cell, or part thereof. The invention also provides a seed that produces a plant in accordance with the invention.

In another embodiment, the invention provides a *Solanum lycopersicum* plant of the invention, wherein a representative sample of seed comprising said chromosomal segment was deposited under ATCC Accession Number PTA-121480. In another embodiment, a *Solanum lycopersicum* plant of the invention comprises a *Solanum peruvianum* allele at locus NSLYC008433769 and a *Solanum peruvianum* allele at locus NSLYC008433807, wherein said plant exhibits improved resistance to *Fusarium* crown and root rot relative to a plant lacking the introgressed genomic region. In another embodiment, a *Solanum lycopersicum* plant of the invention comprises a *Solanum lycopersicum* allele at locus NL0217199, and a *Solanum pennellii* allele at locus NSLYC009229170, wherein the fruit of said plant exhibits elevated Brix levels relative to the fruit of a plant lacking the introgressed genomic region. In still further embodiments, the invention provides a plant part of a *Solanum lycopersicum* plant of the invention. In another embodiment, the part is a leaf, root, flower, fruit, pollen, ovule, seed, cell, or part thereof. In a further embodiment, the invention provides a seed that produces a plant of the invention.

In another aspect, the invention provides a recombined chromosomal segment comprising a Lin5 allele from *Solanum pennellii*, a Fr1 allele from *Solanum peruvianum*, and a Tm2a allele from *S. peruvianum*, which confers improved resistance to *Fusarium* crown and root rot and tomato mosaic virus, and elevated Brix levels relative to a plant lacking said segment when contained in a *Solanum lycopersicum* plant. In one embodiment, the invention provides a plant, seed, cell, or plant part comprising such a recombined chromosomal segment.

In another aspect, the invention provides a method for producing a hybrid *Solanum lycopersicum* plant with improved resistance to *Fusarium* crown and root rot and tomato mosaic virus, and elevated Brix levels, comprising crossing a first *Solanum lycopersicum* parent plant with a second *Solanum lycopersicum* plant of a different genotype, wherein the first parent plant comprises a Lin5 allele from *Solanum pennellii*, a Fr1 allele from *Solanum peruvianum*, and a Tm2a allele from *S. peruvianum*, wherein the Lin5, Fr1, and Tm2a alleles confer improved resistance to *Fusarium* crown and root rot and tomato mosaic virus, and elevated Brix levels relative to a plant lacking the Lin5, Fr1, and Tm2a alleles. In an embodiment, the method further comprises producing a plurality of hybrid *Solanum lycopersicum* plants comprising crossing the first *Solanum lycopersicum* parent plant with a plurality of second *Solanum lycopersicum* plants of different genotypes.

In another aspect, the invention provides a method of producing a *Solanum lycopersicum* plant with improved resistance to *Fusarium* crown and root rot and tomato mosaic virus, and elevated Brix levels, comprising introgressing into the plant a chromosomal segment comprising a Lin5 allele from *Solanum pennellii*, a Fr1 allele from *Solanum peruvianum*, and a Tm2a allele from *S. peruvianum*, wherein said segment confers improved resistance to *Fusarium* crown and root rot and tomato mosaic virus, and elevated Brix levels relative to a plant lacking said segment, and wherein a sample of seed comprising said segment is deposited under ATCC Accession No. PTA-121480.

In another aspect, the invention provides a method of identifying a tomato plant comprising a genotype associated with resistance to *Fusarium* crown and root rot, the method comprising the step of: detecting in said plant at least a first polymorphism in locus NSLYC008433807 or locus NSLYC008433769.

In still another aspect, the invention provides a method of identifying a tomato plant comprising a genotype associated with increased Brix levels in fruit, the method comprising the step of: detecting in said plant at least a first polymorphism in locus NSLYC009194570.

BRIEF DESCRIPTION OF THE DRAWINGS

FIG. 2: Shows haplotype analysis of inbred lines tested for resistance to *Fusarium* crown and root rot (FCRR). R indicates resistant lines and S indicates susceptible lines. Trait-linked genetic markers are indicated in the top row. These markers are ordered, and orientated, left to right. The orientation is such that the markers on the left side are closer to the adjacent Lin5 locus, while the markers on the right side are closer to the adjacent Tm2A locus. LYC indicates the genomic regions originating from *S. lycopersicum*, and PER indicates the genomic regions originating from *S. peruvianum*. Boldface type indicates an event with reduced introgression size which was observed in several lines. Marker NL0241464 is a previously identified marker, while markers NSLYC008433769 and NSLYC008433807 are markers provided by the invention.

FIG. 4: Shows a sequence alignment of the Lin5 gene sequence demonstrating sequences from several sequences lines including two polymorphic Lin5 alleles and a non-Lin5 allele comprising a deletion. The top oval indicates the forward primer and the lower the probe sequence. The arrow points to the causal single nucleotide polymorphism (SNP; A/T). T is the genotype of Lin5 lines (comprised in SEQ ID NO:28, shown in rows 2-5) and A the alternate allele (comprised in SEQ ID NO:29, shown in rows 1, 6-9, and bottom most). The 15 bp deletion present in part of non-Lin5 germplasm is marked by a circle (comprised in SEQ ID NO:30, shown in rows 10-17).

FIG. 6: Shows evaluation of recombinant events in an elite background for presence of the Pen9 interval. Marker Q-NL0247854 is a trait-associated marker. Marker NSLYC009229170 is a novel marker according to the present invention. PEN indicates the *pennellii* allele, ESC indicates the *esculentum* allele, and HET indicates a heterozygous allele.

DETAILED DESCRIPTION

Figure 1:
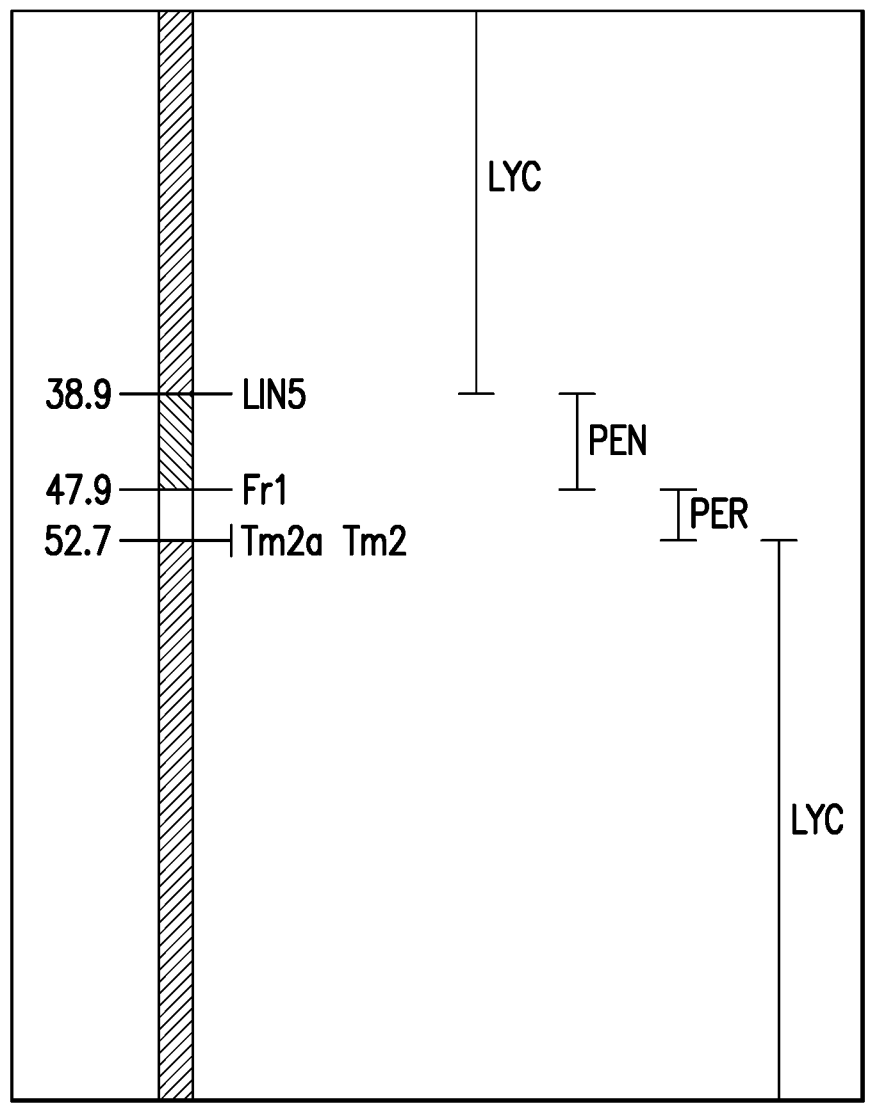
FIG. 1: Shows a simplified genetic map of *S. lycopersicum* chromosome 9 around the recombined introgression event of the present invention comprising Lin5, Fr1 and Tm2a. Genetic distance is shown in cM. LYC=*S. lycopersicum*, PEN=*S. pennellii* and PER=*S. peruvianum*.

The taste of ripe tomato fruit is predominantly determined by sugar and titratable acid content, jointly measured as a sum parameter in degrees Brix. Brix level is determined by both environmental and genetic factors. For example, growers may control the environment to increase Brix by using saline irrigation water with raised electrical conductivity. However, this has been shown to result in reduced fruit yield. Thus, cultivation methods allow growers to increase Brix at harvest point, albeit with a yield penalty.

Among the genetic factors that influence Brix are quantitative trait loci (QTL) controlling fruit size. Examples of size categories distinguished in the market include, from large to small: beef, large, medium, small, and cherry tomato types. Varieties with a lower fruit weight typically have higher Brix (i.e. there is a negative relationship between Brix values and fruit weight).

Methods of increasing Brix level in fruit, or of uncoupling the relationship between lower fruit weight and increased Brix would therefore be of a great benefit to any breeding program. In order to accomplish this, the present invention provides novel and inventive compositions, methods and genetic markers which enable the improvement of Brix in fruit, without compromising the targeted commercial fruit weight.

Work by Eshed & Zamir (1995) describes several Brix increasing genome regions in plants derived from a cross between *Solanum lycopersicum* (formerly named *Lycopersicon esculentum*) and *Solanum pennellii* LA0716. The inventors used these inbred lines to develop elite lines with increased Brix, but without the commercially undesirable lower fruit weight. The inventors have focused their work on two loci, one on chromosome 1 and one on chromosome 9, which both have been described as Brix increasing loci in the literature (Eshed & Zamir 1995, Baxter et. al. 2005).

Alleles responsible for higher Brix levels in fruit can each increase Brix levels significantly. However, on their own these increases are not always perceptible by humans. The increase in Brix has to be 0.6° or higher before a human can detect a taste difference. Because the beneficial effect of brix QTL often fall below the taste perception level of approximately 0.6° brix, it is logical to attempt to deploy Brix loci in combination, in order to obtain an additive effect of the individual QTL loci. However, with the specific brix QTLs on chromosomes 1 (IL1-4) and 9 (IL9-2-5), Eshed and Zamir (FIG. 1 of Eshed & Zamir, 1996) demonstrated that the combination of these two Brix QTL resulted in a Brix increase which is less than additive due to negative epistasis. Not only Brix, but also yield and plant mass were negatively affected by previously texted combinations of Brix loci.

Despite these obstacles to increasing Brix levels in fruit while maintaining acceptable yield, the present inventors were surprisingly able to stack the Pen1 QTL and Lin5 allele from *S. pennellii* (SP_Lin5) in elite *S. lycopersicum* that resulted in additive level or higher levels of Brix depending on the seasonal conditions.

A further consideration in any fruit breeding program is disease resistance, which is critical to maintaining acceptable fruit yield. *Fusarium* crown and root rot (FCRR), and tomato mosaic virus (ToMV), as well as other Tobamoviruses, are damaging diseases. Infection by either pathogen can result in severe fruit yield loss in tomato plants. Despite intensive efforts to introgress genes conferring resistance to FCRR and ToMV from non-cultivated species into elite *Solanum* lines, progress in the field has been impeded by inaccurate markers for tracking disease resistance genes and difficulty in obtaining recombination associated with crosses between genetically diverse lines. In addition, linkage drag has resulted in low fruit quality or necrosis in cultivated tomato lines carrying disease resistance genes from non-cultivated species. Yield loss due to FCRR and ToMV therefore remains a significant problem.

For the first time, the invention provides a novel introgression of disease resistance alleles from *Solanum peruvianum* and fruit quality alleles from *Solanum pennellii* into an elite *Solanum lycopersicum* line. This novel composition of alleles results in tomato plants exhibiting high levels of resistance to FCRR and ToMV and produce fruit with increased Brix levels. The invention further provides novel, markers for accurate tracking of the introgressed alleles during plant breeding. In further embodiments, the invention provides novel Pen1/Fr1/SP_Lin5/Tm2a introgressions conferring increased Brix compared with plants lacking the introgression as well as novel Tm1/Fr1/SP_Lin5/Tm2a introgressions conferring increased resistance to ToMV with reduced necrosis compared with plants lacking the introgression, and markers for tracking the introgressed alleles during plant breeding.

Plants comprising the novel introgression disclosed herein carry the Fr1 disease resistance allele from *S. peruvianum*, the Tm2a disease resistance allele from *S. peruvianum*, and the Lin5 fruit quality allele from *S. pennellii*. Introgression of these alleles into cultivated lines, with or without the use of marker assisted selection, has thus far presented significant problems due to factors such as linkage drag or lack of recombination in crosses between genetically diverse lines. The current invention overcomes this and now provides tomato plants comprising the novel introgression which exhibit resistance to FCRR and ToMV, and higher fruit quality.

Fr1 is a gene found in wild *S. peruvianum* lines which confers resistance to FCRR in a dominant fashion. However, existing markers linked to Fr1 do not correlate with disease scores in some plant lines. The instant disclosure shows for the first time that Fr1 resistance may reside in a tandem repeat of duplicated genes, significantly complicating the identification of accurate markers. Surprisingly, despite tandem repeats in genomic regions associated with Fr1 and limited understanding of the genetic loci controlling FCRR resistance, the invention has succeeded in providing novel, validated markers for predicting the genotypic state, and thus, the predicted phenotypic state for FRCC resistance, that have substantially improved predictive value over previously existing markers. Moreover, although it was previously believed that heterozygous deployment of the Fr1 disease tolerance allele was necessary to reduce negative linkage drag when introgressing Fr1 alleles from wild species, the present invention unexpectedly demonstrates that homozygous deployment of the Fr1 disease resistance allele in plants is acceptable and even preferred for certain fruit types and environments.

The Tm2a gene derived from *S. peruvianum* confers resistance to ToMV when introgressed into plants. However, commercial tomato varieties heterozygous for Tm2a disease resistance alleles show early necrotic symptoms when compared with similar lines that contain the susceptible allele. Contrary to the belief in the field that heterozygous deployment of Tm2a alleles derived from *S. peruvianum* in an elite line was necessary to avoid negative traits such as necrosis due to linkage drag, the present invention surprisingly shows that homozygous deployment of Tm2a alleles reduces necrotic symptoms in plants.

The Lin5 gene, comprised within the Pen9 introgression originating from *S. pennellii*, increases Brix levels in tomato fruit, thereby increasing fruit quality. While the Lin5 gene has been cloned and the polymorphism causal for elevated Brix levels has been identified, existing assays have failed to reproducibly identify the Lin5 allele associated with fruit quality in some genetic backgrounds. The present disclosure unexpectedly identifies a deletion in some plant lines which results in inaccurate detection of the causal polymorphism using existing assays. The invention further provides a novel trait-linked marker based on a previously unknown polymorphism which enables selection for Lin5 alleles in crosses in any type of germplasm. This novel marker will therefore allow breeders to select lines with a Lin5 introgression conferring increased Brix potential at the seedling stage, as opposed to sampling fruits of mature plants.

Moreover, the present invention provides a newly identified SP_Lin5 introgression with a smaller size than the previously-identified Pen9 introgression. Surprisingly, this reduced introgression is highly effective in conferring increased Brix levels in fruit while reducing linkage drag associated with the larger Pen9 introgression. The novel SP_Lin5 introgression provided by the invention therefore improves fruit quality by increasing Brix while beneficially reducing the introduction of negative agronomic traits when the Lin5 gene is introgressed from non-cultivated species into an elite background. Surprisingly, it was also found that homozygous deployment of SP_Lin5 in the plants of the present invention did not result in linkage drag, despite its origin from *S. pennellii*.

The invention further provides novel markers and assays which more accurately identify and track the genomic regions provided herein during plant breeding. Because suppressed recombination is often observed in crosses between genetically diverse *Solanum* lines, conventional breeding methods would require prohibitively large segregating populations for progeny screens. MAS is therefore essential for effective plant breeding. The present invention enables MAS by providing improved and validated markers for detecting genotypes associated with disease resistance and high fruit quality without the need to grow large populations of plants to maturity in order to observe the phenotype.

I. Genomic Regions, Alleles, and Polymorphisms Associated with Fruit Quality and Disease Tolerance in Tomato Plants Applicants have provided herein novel introgressions of one or more alleles associated with fruit quality and disease resistance in tomato plants, together with polymorphic nucleic acids and linked markers for tracking the introgressions during plant breeding.

In some embodiments, the invention provides plants comprising one or more introgressed genomic regions associated with increased Brix in fruit. For example, plants comprising a Lin5 allele from *Solanum pennellii* and a Pen1 allele from *Solanum pennellii*, wherein said plant exhibits elevated Brix levels relative to a plant lacking the Lin5 and Pen1 alleles from *S. pennellii*, are provided. In certain embodiments, the invention provides plants comprising a Lin5 allele and a Pen1 allele, wherein the Brix increase is additive or more than additive compared with the Brix increases seen in fruit from plants containing the individual alleles.

In particular embodiments, the invention further provides introgressed genomic regions comprising Fr1, Tm2a, and Lin5 alleles on chromosome 9 of tomato (FIG. 1). Fr1 alleles derived from *S. peruvianum* confer resistance to FCRR caused by *Fusarium oxysporium* fsp. *radicis lycopersici*. Tm2a alleles originating from *S. peruvianum* provide resistance to ToMV isolates 0, 1 and 2. The Lin5 gene, contained within the SP_Lin5 introgression, elevates the Brix level when introgressed from *S. pennellii* into cultivated tomato.

Although Fr1, Tm2a, and Lin5 have been individually identified in non-cultivated lines, Applicants have overcome significant obstacles in providing a linkage event comprising specific alleles of these genes and conferring beneficial agronomic properties. The development of optimized assays for genotyping plants required the development of recombinants comprising individual Fr1, Tm2a, and Lin5 loci and the re-sequencing of proprietary lines.

A. Introgression of Fr1 Alleles into Cultivated Lines

Efforts to introgress Fr1 resistance alleles into cultivated lines were complicated by the fact that previously existing markers for Fr1 did not correlate with disease scores in all plant lines, with lines that were shown to be susceptible scoring resistant in the marker assay. Applicants have discovered that Fr1 resistance likely resides in a tandem repeat of duplicated genes that are not of the canonical type composed of nucleotide-binding and leucine rich repeat domains. Surprisingly, despite the presence of tandem repeats which considerably complicated marker design and efforts to introgress Fr1 alleles, Applicants were able to develop genetic markers highly correlated with disease resistance in plants.

Using the improved genetic markers and assays of the invention, Applicants were able to successfully identify a novel, truncated introgression of the *S. peruvianum* genomic region comprising Fr1 which effectively confers disease resistance in an elite background while reducing negative linkage drag observed with larger introgressions.

A further obstacle to the successful development of the linkage event of the present invention was the belief in the field that homozygous deployment of introgressed Fr1 disease resistance alleles in cultivated lines would result in unacceptable expression of damaging phenotypes due to linkage drag. Contrary to this belief in the art, Applicants have surprisingly demonstrated that homozygous deployment of the Fr1 alleles of the present invention is tolerated and even preferred for certain fruit types and environments. In particular, the reduced Fr1 introgression of the present invention can be deployed in a homozygous condition without unacceptable levels of linkage drag.

The invention therefore provides newly identified genomic regions from *S. peruvianum* comprising Fr1 disease resistance alleles, novel genetic markers and assays genetically linked to Fr1 alleles in plants, and plants comprising novel introgressions of Fr1 alleles from *S. peruvianum* exhibiting improved tolerance to FCRR compared with plants not comprising the introgressed Fr1 alleles. In some embodiments, the Fr1 alleles of the invention are contained within a novel linkage event comprising additional alleles providing beneficial traits, such as Tm2a and Lin5. Other embodiments of the invention provide novel markers NSLYC008433807 and NSLYC008433769 which have been shown to be genetically linked to Fr1 disease resistance alleles in plants. Novel assays for detecting these markers are further provided by the invention. For example, alleles at marker NSLYC008433807 can be detected using primers having SEQ ID NOs: 1 and 2, and by probes having SEQ ID NOs: 3 and 4. In another example, alleles at marker NSLYC008433769 can be detected using primers having SEQ ID NOs: 5 and 6, and by probes having SEQ ID NOs: 7 and 8.

B. Introgression of Tm2a Alleles into Cultivated Lines

Efforts to introgress Tm2a alleles associated with resistance to ToMV into cultivated lines were similarly complicated by the belief in the field that homozygous deployment of Tm2a would result in unacceptable levels of early necrosis in plants due to linkage drag from non-cultivated lines. In particular, it was believed that heterozygous deployment of this dominant gene was necessary to avoid negative drag associated with genomic regions derived from *S. peruvianum*. However, Applicants have surprisingly demonstrated that homozygous deployment of Tm2a disease resistance alleles is tolerated and even preferable for certain fruit types and conditions.

The invention therefore provides newly identified genetic elements from *S. peruvianum* comprising Tm2a disease resistance alleles which can be deployed homozygously without unacceptable levels of linkage drag. In some embodiments, the Tm2a alleles of the invention are contained within a novel linkage event comprising additional alleles providing beneficial traits, such as Fr1 and Lin5. The invention further provides plants homozygous for the Tm2a disease resistance gene, which exhibit reduced necrosis when compared with plants heterozygous for Tm2a. The finding that homozygous deployment of Tm2a disease resistance alleles actually reduced necrosis was unexpected and runs contrary to conventional understanding.

C. Introgression of SP_Lin5 Alleles into Cultivated Lines

When attempting to introgress SP_Lin5 fruit quality alleles into cultivated lines, Applicants unexpectedly discovered that existing markers for the cloned Lin5 gene were not predictive in every genetic background, despite being designed to interrogate a SNP within the Lin5 gene which is causal for Brix increase. Despite discovering an Indel polymorphism in the Lin5 gene which further complicated marker design, Applicants were able to discover improved markers for SP_Lin5 which were predictive of high Brix levels in fruit.

Moreover, Applicants identified a novel, truncated introgression of a genomic region from *S. pennellii* comprising Lin5 alleles that provided increased Brix levels in fruit while reducing linkage drag associated with larger introgressions. Reduced introgressions such as the SP_Lin5 introgression disclosed herein are essential for mitigating linkage drag when introducing genes from wild species into cultivated lines.

Finally, it was unexpectedly found that homozygous deployment of the reduced SP_Lin5 introgression of the present invention does not result in linkage drag in tomato types for heated cultivation, despite its origin from *S. pennellii*.

The invention therefore provides plants comprising a novel reduced introgression comprising SP_Lin5, which results in higher levels of Brix in fruit compared with plants lacking the Lin5 gene from *S. pennellii*. In some embodiments, the Lin5 alleles of the invention are contained within a novel linkage event comprising additional alleles providing beneficial traits, such as Fr1 and Tm2a. The invention further provides improved markers genetically linked to Lin5 alleles associated with increased Brix levels in tomatoes. For example, markers NSLYC009194570, NL0217199, and NSLYC009229170 have been identified and shown to correlate with Brix levels in fruit. For example, alleles at marker NSLYC009194570 can be detected using primers having SEQ ID NOs: 9 and 10, and by probes having SEQ ID NOs: 11 and 12. In another example, alleles at marker NL0217199 can be detected using primers having SEQ ID NOs: 13 and 14, and by probes having SEQ ID NOs: 15 and 16. In yet another example, alleles at marker NSLYC009229170 can be detected using primers having SEQ ID NOs: 17 and 18, and by probes having SEQ ID NOs: 19 and 20.

D. A Novel Linkage Event Comprising Fr1, Tm2a, and Lin5 Alleles

In further embodiments, the invention provides a novel linkage event comprising one or more of the genomic regions from *S. peruvianum* or *S. pennellii* disclosed herein. In certain embodiments, the novel linkage event of the present invention comprises genomic regions from *S. peruvianum* or *S. pennellii* comprising one or more Fr1, Tm2a, and Lin5 alleles. The invention further includes a novel linkage event comprising Fr1, Tm2a, and Lin5 alleles identified herein, and in some embodiments provides alleles of Fr1, Tm2a, and Lin5 which may be deployed homozygously without negative linkage drag such as early necrosis or low fruit quality. The invention further provides markers for identifying and tracking introgressed genomic regions from *S. peruvianum* or *S. pennellii* comprising one or more Fr1, Lin5, and Tm2a alleles in a plant. In certain embodiments, markers NSLYC008433807 and NSLYC008433769 for identifying Fr1 alleles in plants, and markers NSLYC009194570, NL0217199, and NSLYC009229170 for identifying Lin5 alleles in plants are provided.

The above genomic regions, introgressions, and markers are exemplary. Given the present disclosure, one of skill in the art would recognize how to develop other introgressions comprising the specific genomic regions comprising Fr1, Tm2a, and Lin5 identified herein or the recombed linkage event provided herein. A person of skill in the art would further recognize how to identify additional markers for identifying the novel introgressions of the invention in plants using the instant disclosure.

II. Introgression of Recombined Genomic Regions Associated with Fruit Quality and Disease Tolerance Marker-assisted introgression involves the transfer of a chromosomal region defined by one or more markers from a first germplasm to a second germplasm. Offspring of a cross that contain the introgressed genomic region can be identified by the combination of markers characteristic of the desired introgressed genomic region from a first germplasm and both linked and unlinked markers characteristic of the desired genetic background of a second germplasm.

The present invention therefore provides novel markers for identifying and tracking introgression of one or more of the genomic regions from *S. peruvianum* or *S. pennellii* disclosed herein into cultivated lines. In certain embodiments, the markers of the present invention are linked to genomic regions from *S. peruvianum* or *S. pennellii* comprising Fr1, Tm2a, and Lin5 alleles. The invention further provides markers for identifying and tracking the novel linkage event disclosed herein during plant breeding, for example markers NSLYC008433807 and NSLYC008433769 for identifying Fr1 alleles in plants, markers NSLYC009194570, NL0217199, and NSLYC009229170 for identifying Lin5 alleles in plants, and marker NSLYC005704029 at around 6.1 cM distance from the Brix increasing allele for identifying Pen1 alleles in plants.

Markers within or linked to any of the genomic intervals of the present invention may be useful in a variety of breeding efforts that include, but are not limited to, introgression of genomic regions associated with disease tolerance or fruit quality into a desired genetic background. For example, a marker within 40 cM, 20 cM, 15 cM, 10 cM, 5 cM, 2 cM, or 1 cM of a marker associated with disease tolerance or fruit quality described herein can be used for marker-assisted introgression of genomic regions associated with a disease tolerant or high fruit quality phenotype.

Tomato plants comprising one or more introgressed regions associated with a desired phenotype wherein at least 10%, 25%, 50%, 75%, 90%, or 99% of the remaining genomic sequences carry markers characteristic of the germplasm are also provided. Tomato plants comprising an introgressed region comprising regions closely linked to or adjacent to the genomic regions and markers provided herein and associated with a disease resistance and high fruit quality phenotype are also provided.

III. Development of Disease Resistant Tomato Varieties Having Elevated Brix Levels in Fruit For most breeding objectives, commercial breeders work within germplasm that is "cultivated type" or "elite," i.e., a commercial variety. This germplasm is easier to breed because it generally performs well when evaluated for horticultural performance. For example, *S. lycopersicum* is an agronomically elite, cultivated tomato adapted to commercial use. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. In tomato plants, non-cultivated types such as *S. peruvianum* or *S. pennellii* can provide alleles associated with disease resistance or desirable fruit qualities. However, these non-cultivated types may have poor horticultural qualities such as vulnerability to necrosis or low fruit production.

The process of introgressing desirable resistance genes from the non-cultivated lines into the elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance and fruit quality. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease tolerance or fruit quality disclosed herein can be introgressed from one genotype to another and tracked using MAS. Thus, Applicants' discovery of accurate markers associated with disease resistance and fruit quality will facilitate the development of tomato plants having beneficial phenotypes.

For example, seed can be genotyped using the markers of the present invention in order to select for plants comprising desired genomic regions associated with disease tolerance or fruit quality. Moreover, MAS allows identification of plants homozygous or heterozygous for a desired introgression. In one embodiment of the present invention, MAS allows selection of plants homozygous for Fr1, Tm2a, and Lin5, which is surprisingly shown in the instant disclosure to provide improved disease resistance and elevated Brix levels in tomato plants while reducing necrosis.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the separation of adjacent deleterious genomic fragments from the favorable trait genomic fragment, and pyramiding traits that are genetically tightly linked. Therefore, in the absence of accurate markers, suppressed recombination forces breeders to enlarge segregating populations for progeny screens.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among *Solanum* species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics*, 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques*, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a tomato plant a genotype associated with disease tolerance or high fruit quality, identify a tomato plant with a genotype associated with disease tolerance or high fruit quality, and to select a tomato plant with a genotype associated with disease tolerance or high fruit quality. In certain embodiments of methods of the invention, polymorphic nucleic acids can be used to produce a tomato plant that comprises in its genome an introgressed locus associated with disease tolerance or high fruit quality. In certain embodiments of the invention, polymorphic nucleic acids can be used to breed progeny tomato plants comprising a locus associated with disease tolerance or high fruit quality.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease tolerance or high fruit quality in tomato plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' 3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, "Lin5" or "lin5" is intended to refer to the gene on chromosome 9 that regulates/affects Brix in tomato plants, and "Pen9" or "pen9" is intended to refer to the QTL/introgression from *S. pennellii* that contains the lin5 gene that increases Brix.

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

V. Deposit Information

A deposit was made of at least 2500 seeds of tomato line NE7466-B, which comprises a linkage event comprising Fr1 and Tm2a alleles from *S. peruvianum* and a Lin5 allele from *S. pennellii*, as described herein. The deposit was made with the American Type Culture Collection (ATCC), 10801 University Boulevard, Manassas, Va. 20110-2209 USA. The deposit is assigned ATCC Accession No. PTA-121480, and the date of deposit was Aug. 13, 2014. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

Example 1

Development of Improved Markers for Fr1 and Identification of Candidate Genes

FCRR is a root disease in tomato caused by *Fusarium oxysporum* fsp. *radicis lycopersici*. *S. peruvianum*, which occurs in the wild, appeared to contain Fr1, a dominant resistance gene against FCRR. A trait-linked marker was therefore developed. However, marker alleles did not correlate with disease scores in a subset of the germplasm, and lines that were shown to be susceptible scored resistant in the marker assay.

In order to develop a precise and accurate assay for indirect selection, a line panel was re-sequenced. The panel included inbreds without resistance, lines carrying Fr1, lines carrying Tm2a, and lines carrying a combination of Fr1 and Tm2a. Sequencing primers were designed in the vicinity of Fr1 with Primer3® software (SimGene), based on the tomato genome sequence. Amplification products of 1.0 to 1.6 kb were generated, spaced apart one million base pairs (Mbp) in an interval of 6 Mbp. PCR products were amplified using standard conditions, labeled with Big Dye Direct® sequencing kit (Life Technologies) and analyzed on the ABI 3130×1 sequencer (Applied Biosystems). DNA sequence fragments were assembled using Sequencher DNA sequence analysis software (Gene Codes).

Nucleotides that were polymorphic between phenotypic classes were used for assay development. Additionally, primers for amplifying annotated genes (annotated at solgenomics.net) with a putative role in disease resistance were designed in the vicinity of Fr1. Based on marker NSLYC008433807 that showed good correlation between resistant and susceptible lines, Fr1 fine-mapped to an interval between 4.5 and 5.2 Mbp. This marker was located 214 kb north of a previously identified marker. No false positives were observed, however, false negatives (i.e. resistant lines that scored susceptible with the marker) were detected.

As a next step, single nucleotide polymorphisms (SNPs) that were polymorphic between a sequenced resistant tomato line and two sequenced susceptible lines, HEINZ1706 and Moneyberg, were used to develop TaqMan assays within the identified 214 kb region. TaqMan assays were also developed by re-sequencing fragments in the same interval, mainly fragments of annotated genes.

Analysis of the data resulted in one marker assay (NSLYC008433807) that passed precision and accuracy tests based on more than 97% correlation in the germplasm panel. In contrast, other trait linked markers NL0241464 and NSLYC008433769 showed correlations of only 81 and 90%, respectively. The haplotype analysis also characterized various recombination events between *S. lycopersicum* (LYC) and *S. peruvianum* (PER). An event with reduced introgression size was discovered in several lines (FIG. 2, lines in boldface type).

TaqMan assays using markers NSLYC008433807 and NSLYC008433769 were designed based on the sequence polymorphisms identified, as shown in Table 1.

TABLE 1

SEQ ID NOs for NSLYC008433807 and NSLYC008433769 marker assays.

| Marker Name | Forward Primer Sequence | Reverse Primer Sequence | VIC Probe Sequence | FAM Probe Sequence |
|---|---|---|---|---|
| NSLYC008433807 | 1 | 2 | 3 | 4 |
| NSLYC008433769 | 5 | 6 | 7 | 8 |

PCR reactions were carried out in a 5 µl reaction, with 2.5 µl 2×Taqman GTXpress Master mix (Life Technologies) and 0.063 µl 80×Taqman assay mix (Life Technologies). The reaction is performed for 1 cycle of 20 seconds at 94° C., followed by 40 cycles of 3 seconds at 94° C. and 20 seconds at 60° C.

Figure 3:
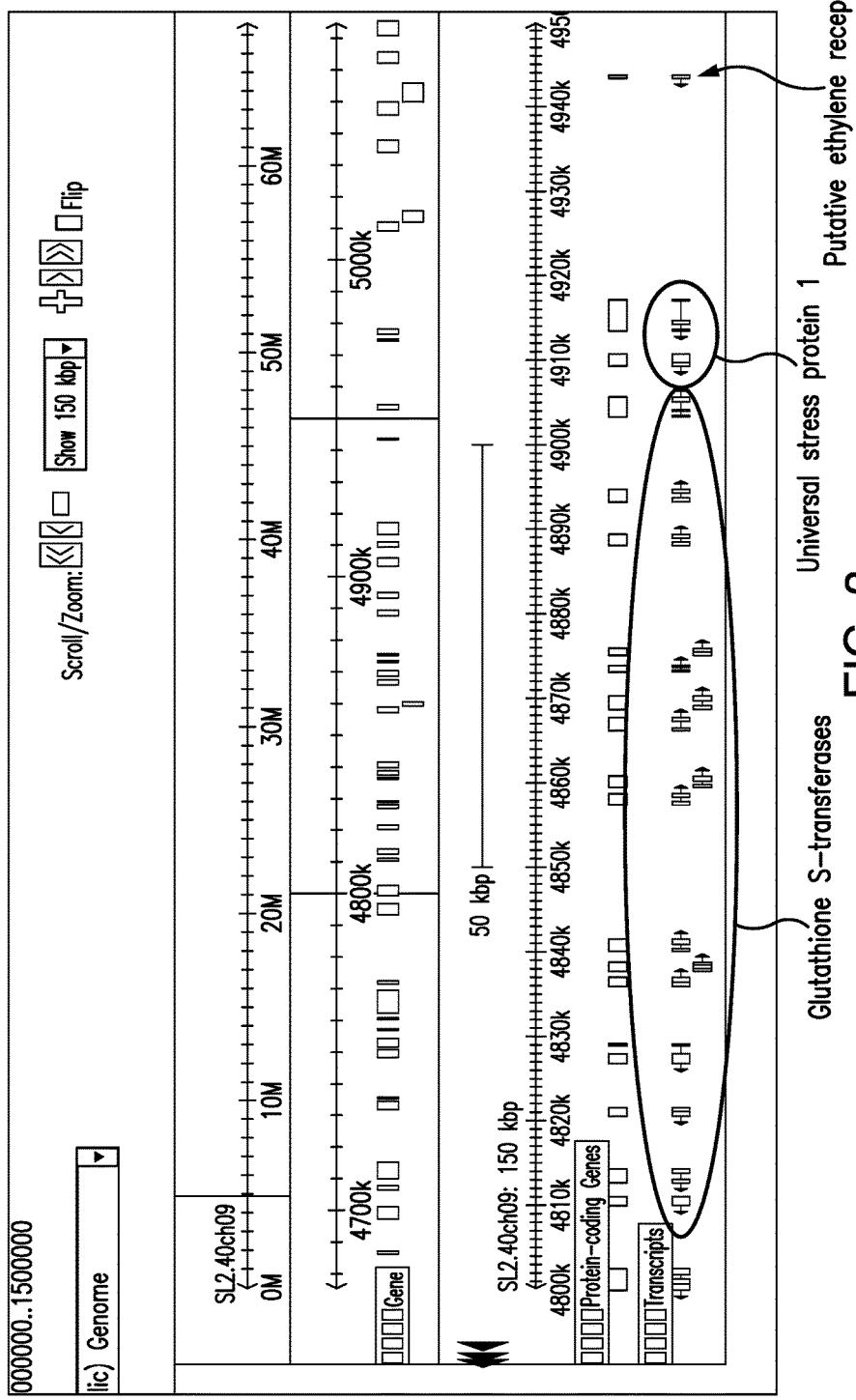
FIG. 3: Shows an image of annotated genes with the identified Fr1 interval displayed using the publically available Generic Genome Browser (GBrowse). The large oval highlights sixteen copies of the glutathione S-transferase (GST) gene. The smaller circle indicates universal stress protein 1, and the arrow indicates a putative ethylene receptor.

The identified Fr1 interval encompasses annotated genes. One potential gene candidate is glutathione S-transferase (GST), which is involved in pathogen defense. Sixteen different gene copies of GST exist at the Fr1 locus. It is unknown which copy confers resistance, or which homologues are active. However, GST family members represent the strongest candidates for Fr1, because two copies of Universal Stress Protein 1 in the interval are likely involved abiotic stress response and a third gene is annotated as an ethylene receptor. FIG. 3 demonstrates the relative positions of annotated genes within the Fr1 interval.

Example 2

Development of Improved Markers for Lin5

Figure 4:
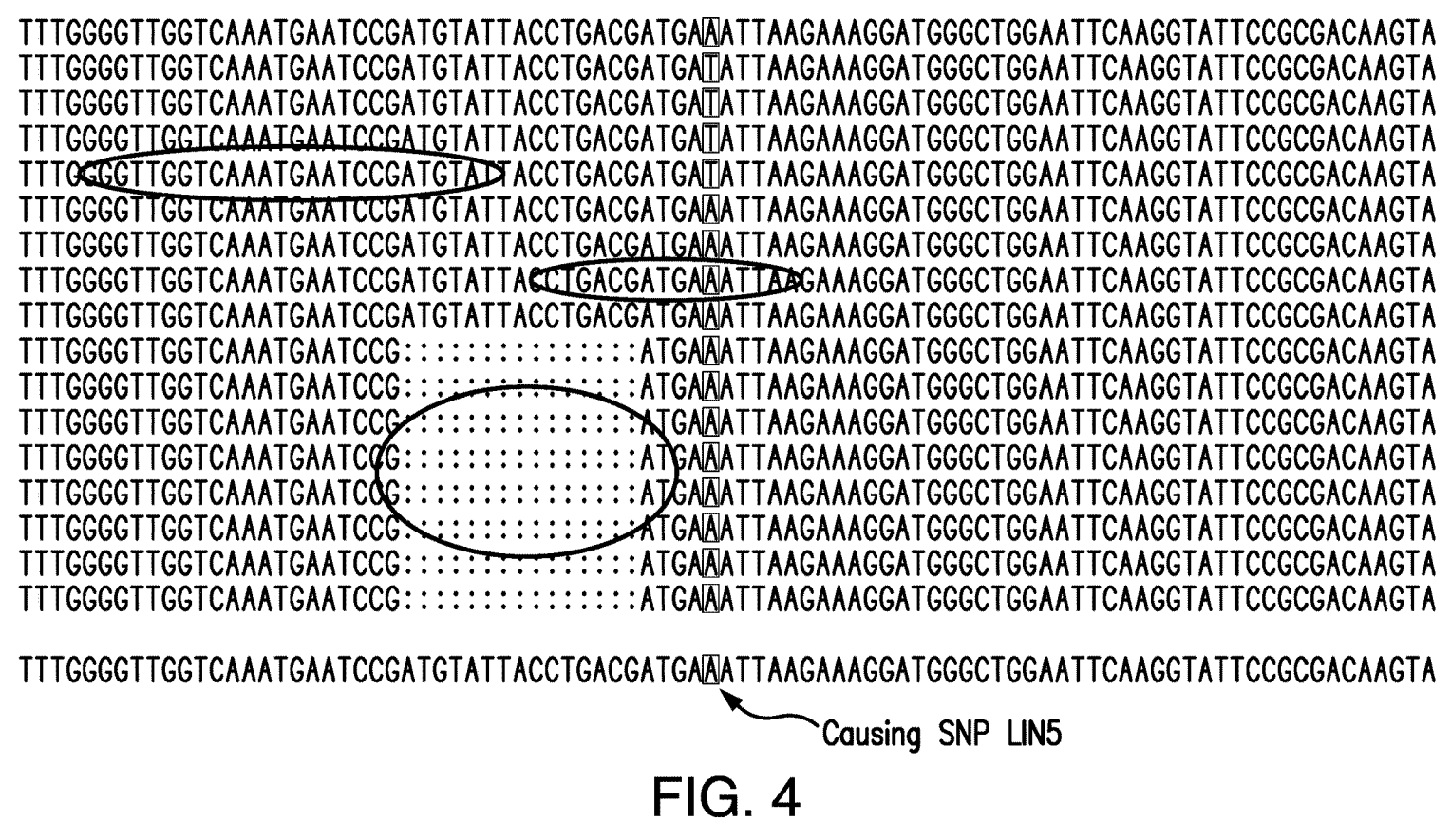

The gene Pen9 introgression, comprising the Lin5 gene, originates from Solanum pennellii LA716 and increases Brix levels in tomato fruit. Lin5 has been cloned and the causal SNP identified (Zanor, et al., Plant Phys, 2009, 150:1204). However, a TaqMan assay specifically interrogating this SNP did not produce a signal in a subset of the germplasm. Experiments were therefore carried out to determine whether the sequence recognized by the probe was not amplified due to an insertion/deletion (Indel) event disrupting the recognition site. Primer pairs were designed based on the Lin5 sequence and lines with the favorable or alternate alleles were re-sequenced together with lines that appeared to lack Lin5 completely (non-Lin5). Sequence analysis confirmed a 15 bp deletion in lines appearing to lack Lin5, located 5 bp before the causal SNP. The deletion influenced annealing of both the probe and forward primer because the first six nucleotides of the probe were not complementary to the template. The same was true for the final six nucleotides of the forward primer. As a result, no amplification product was formed (FIG. 4).

A new TaqMan assay was developed based on a guanine/adenine polymorphism located 80 bp upstream of the causal SNP. This new TaqMan marker was designated NSLYC009194570 and validated as new trait linked marker for SP_Lin5. The new TaqMan assay enables selection for the Lin5 allele from S. pennellii in crosses in any type of germplasm. This novel marker and assay will therefore allow breeders to select lines with an increased Brix potential at the seedling stage, as opposed to sampling fruits of mature plants.

A TaqMan assay (NSLYC009194570) was designed based on one of the sequence polymorphisms identified, as shown in Table 2.

TABLE 2

SEQ ID NOs for NSLYC009194570 marker assay.

| Marker Name | Forward Primer Sequence | Reverse Primer Sequence | VIC Probe Sequence | FAM Probe Sequence |
|---|---|---|---|---|
| NSLYC009194570 | 9 | 10 | 11 | 12 |

PCR reactions were carried out in a 5 µl reaction, with 2.5 µl 2×Taqman GTXpress Master mix (Life Technologies) and 0.063 µl 80×Taqman assay mix (Life Technologies). The reaction is performed for 1 cycle of 20 seconds at 94° C., followed by 40 cycles of 3 seconds at 94° C. and 20 seconds at 60° C.

Example 3

SP_Lin5 Event Creation

Figure 5:
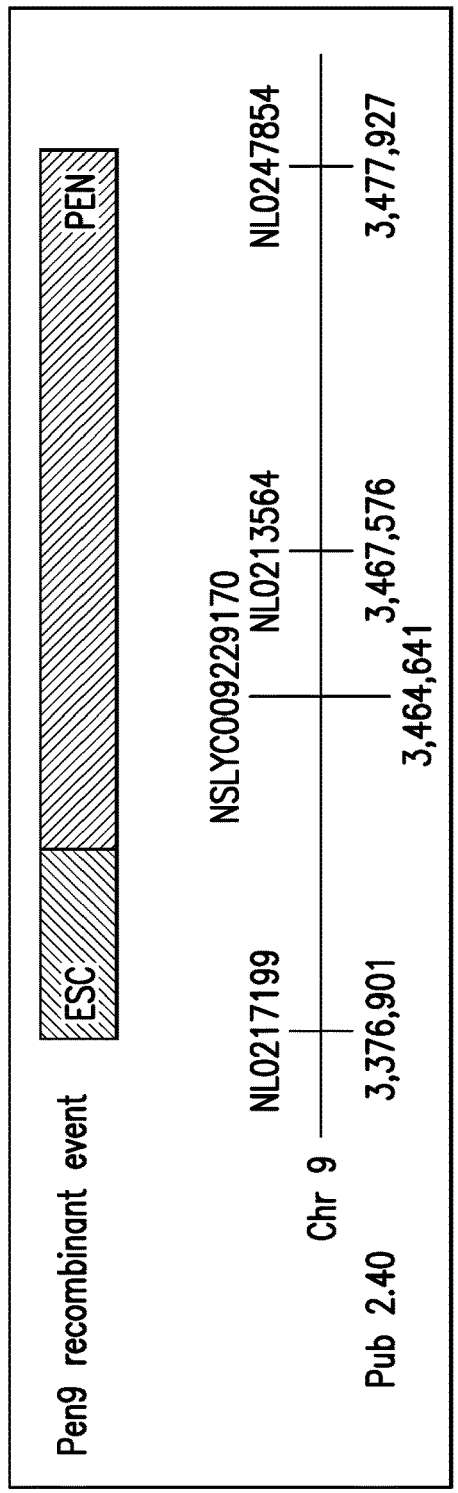
FIG. 5: Shows the Pen9 recombinant interval showing markers used to evaluate the recombinant event. Map positions are from the public physical map v2.40 (The Tomato Genome Consortium, Nature 485 (2012), 635-641, doi: 10.1038/nature11119).

As described in Example 2, the Lin5 gene is known to be causal for Brix increase and originates from S. pennellii. A smaller introgression from this source is highly preferred to reduce the risk of linkage drag. Recombinant events were identified and evaluated for the favorable genotype in elite background. The markers used to evaluate the recombinant event are shown in FIG. 5. The SP_Lin5 interval is shown with map positions from public physical map v2.40 (The Tomato Genome Consortium, Nature 485 (2012), 635-641, doi:10.1038/nature11119). FIG. 6 shows the genotypic values for each family used in the experiment.

TaqMan assays for markers NL0217199 and NSLYC009229170 were designed based on one of the sequence polymorphisms identified, as shown in Table 3.

TABLE 3

SEQ ID NOs for NL0217199 and NSLYC009229170 marker assays.

| Marker Name | Forward Primer Sequence | Reverse Primer Sequence | Probe 1 Sequence | Probe 2 Sequence |
|---|---|---|---|---|
| NL0217199 | 13 | 14 | 15 | 16 |
| NSLYC009229170 | 17 | 18 | 19 | 20 |

To test the performance and efficacy of the recombinant event in an elite background, trials were performed with the genotypes shown in FIG. 6 in Bergschenhoek, the Netherlands. Trials were conducted in a single greenhouse compartment, with seedlings planted twenty days after sowing. Fruit quality traits (e.g. Brix, sugars) were measured two times during the season, referred to as Harvest 1 and Harvest 2.

Data were entered into JMP® software (SAS, Carey, N.C.) and analyzed. The homozygous, reduced interval from S. pennellii appeared to give a significant Brix increase of 0.87-0.97 relative to the S. lycopersicum control. Although the Harvest 2 p-value did not meet the 0.05 cutoff for significance, it was quite close (0.062) and highly suggestive of a significant difference. The same comparisons were conducted for total sugars and titratable acids (Table 4 and Table 5). The increase of sugars was observed for the homozygous recombinant compared to S. lycopersicum control for both harvests. In addition, the full Pen9 interval compared to the S. lycopersicum interval is significant. Finally, drag with the reduced Pen9 introgression fragment was removed (Table 7).

TABLE 4

Pair wise t-test results comparing total sugar levels between SP_Lin5 (Pen9_rec_hom)
homozygous recombinant plants, the non-recombinant (*S. lycopersicum*) sister lines
(Pen9_null) and the control plants with the larger Pen9 introgression (Pen9_control).

| | | Total Sugars | | | | | | |
|---|---|---|---|---|---|---|---|---|
| | | HARVEST 1 | | | | HARVEST 2 | | |
| Plot | Genotypes | Pvalue | Delta | LSM | Pattern | Pvalue | Delta | LSM | Pattern |
| 13TJD0301 | Pen9_rec_hom | 0.0127 | 0.461823 | 2.43 | Pen rec > Esc | 0.0242 | 0.639356 | 2.82 | Pen rec > Esc |
| 13TJD0300 | Pen9_null | | | 1.97 | | | | 2.18 | |
| 13TJD0303 | Pen9_control | 0.0146 | 0.448149 | 2.42 | Pen full > Esc | 0.1011 | 0.413269 | 2.59 | |
| 13TJD0300 | Pen9_null | | | 1.97 | | | | 2.18 | |
| 13TJD0301 | Pen9_rec_hom | 0.9269 | 0.013674 | 2.43 | | 0.3304 | 0.226086 | 2.82 | |
| 13TJD0303 | Pen9_control | | | 2.42 | | | | 2.59 | |

TABLE 5

Pair wise t-test results comparing titratable acidity (pH 8.2) levels
between SP_Lin5 (Pen9_rec_hom) homozygous recombinant
plants, the non-recombinant (*S. lycopersicum*) sister lines (Pen9_null)
and the control plants with the larger Pen9 introgression
(Pen9_control). Like total sugars, titratable acidity also increases in
plants carrying the SP_Lin5 introgression.

| | | HARVEST 1 | | | |
|---|---|---|---|---|---|
| Plot | Genotypes | Pvalue | Delta | LSM | Pattern |
| 13TJD0301 | Pen9_rec_hom | 0.0414 | 1.022667 | 6.04 | Pen |
| 13TJD0300 | Pen9_null | | | 5.02 | rec > Esc |
| 13TJD0303 | Pen9_control | 0.1327 | 0.705333 | 5.73 | |
| 13TJD0300 | Pen9_null | | | 5.02 | |
| 13TJD0301 | Pen9_rec_hom | 0.473 | 0.317333 | 6.04 | |
| 13TJD0303 | Pen9_control | | | 5.73 | |

TABLE 6

Pair wise t-test results comparing linkage drag trait between SP_Lin5
(Pen9_rec_hom) homozygous recombinant plants, the
non-recombinant (*S. lycopersicum*) sister lines (Pen9_null)
and the control plants with the larger Pen9 introgression
(Pen9_control) When a significant difference in a trait score was
observed, the presence of the *S. pennellii* segment resulted in
reduced drag.

| | | Chlorosis | | | |
|---|---|---|---|---|---|
| Plot | Genotypes | Pvalue | Delta | LSM | Pattern |
| 13TJD0301 | Pen9_rec_hom | 0.0121 | −1.4 | 3.6 | Pen < Esc |
| 13TJD0300 | Pen9_null | | | 5.0 | |
| 13TJD0303 | Pen9_control | 0.1918 | 0.749093 | 5.7 | |
| 13TJD0300 | Pen9_null | | | 5.0 | |
| 13TJD0301 | Pen9_rec_hom | 0.0003 | −2.19354 | 3.6 | Pen |
| 13TJD0303 | Pen9_control | | | 5.7 | rec < Pen full |

In conclusion, the event comprising SP_Lin5 showed a significant increase in Brix and also showed significant increases in total sugars and titratable acidity (TA; pH 8.2). In addition, SP_Lin5 showed similar values for linkage drag traits and even reduced values for chlorosis compared to the *S. lycopersicum* control. Plants with SP_Lin5 showed a significant reduction of linkage drag traits compared to plants with the larger Pen9 introgression.

Example 4

A Deployment Model for the Tm2a Locus

Resistance to the ToMV is governed by three genes (Shi, et al., *Am J. Pl. Sci.*, 2011, 2:180-189). Public entries carrying Tm1 include Master no 2 and NAK 83, and markers linked to Tm1 are described by Arens et al., (*Theor Appl Genet* 120(3):655-664, 2010). The Tm2a gene, which is allelic to Tm2, is typically deployed in commercial varieties because it provides resistance to ToMV strains 0, 1, 2 and 1-2 (Table 7).

TABLE 7

Interactions among Tm alleles and ToMV strains. R =
resistant and S = susceptible.

| | | Strain ToMV | | | | |
|---|---|---|---|---|---|---|
| Genotype | Source | 0 | 1 | 2 | 1-2 | 2a |
| Susceptible | Moneyberg | S | S | S | S | S |
| Tm1 | Mobaci | R | S | R | S | S |
| Tm2 | Moperou | R | R | S | S | S |
| Tm2a | Momor | R | R | R | R | S |

In practice, commercial varieties deploy the Tm2a gene in heterozygous condition. This translates to resistance to races ToMV 0, 1 and 2. However, commercial varieties heterozygous for the Tm2a gene (Tm2al+) may show necrotic symptoms when growers cultivate susceptible varieties nearby. The deployment model of Tm2a was investigated to reduce necrotic symptoms in hybrids. Combinations with Tm2a and other Tm genes were studied in homozygous and heterozygous phase in a Moneyberg background.

Necrosis was observed very early to late in the crop cycle, and was possibly dependent on virus titer used for artificial infection. The allelic genes Tm2 and Tm2a were both very sensitive to necrosis when present in the heterozygous phase (Table 8). Any combination of two distinct Tm genes showed an improved response to necrosis when compared to Tm2a/+. For example, a combination of Tm2a with Tm1 resulted in a fully resistant reaction for ToMV0 and ToMV2 in the absence of necrosis. However, it was clear that homozygous deployment of Tm2a provided the best result to reduce necrotic symptoms. Thus, homozygous deployment of Tm2a offers important benefits relative to heterozygous deployment.

TABLE 8

Interactions among genotypes carrying Tm resistance genes and ToMV strains.

| | strain | | |
|---|---|---|---|
| Gene | ToMV0 | ToMV1 | ToMV2 |
| Tm1/Tm1 | Intermediate resistance (IR) | Susceptible | Resistance |
| Tm2/Tm2 | Late Necrosis | Resistance | Susceptible |
| Tm2a/Tm2a | Late Necrosis | Resistance | Resistance |
| Tm1/+ | Susceptible to IR | Susceptible | Susceptible to IR |
| Tm2/+ | Mid-cycle Necrosis | Mid-cycle Necrosis | Susceptible |
| Tm2a/+ | Early Necrosis | Early Necrosis | Mid-cycle Necrosis |
| Tm1/+ Tm2/+ | Resistance | Mid-cycle Necrosis | Late Necrosis |
| Tm1/+ Tm2a/+ | Resistance | Early Necrosis | Resistance |
| Tm2/+ Tm2a/+ | Mid-cycle Necrosis | Mid-cycle Necrosis | Early Necrosis |

Example 5

Recombination Events Between the Tm2a and SP_Lin5 Loci

The genetic distance between SP_Lin5 and Tm2a is approximately 15 cM. Five elite inbred lines of indeterminate truss type were selected for heated cultivation. The elite inbreds were homozygous for the Tm2a locus that confers resistance to ToMV, and crossed to a homozygous SP_Lin5 donor line lacking Tm2a. Individual F1 plants were selfed and advanced to the F2 generation. A subset of 96 plants of each F2 population was pre-screened with markers linked to SP_Lin5 and ToMV resistance. Among 480 F2 individuals, 8 putative recombinants were identified (Table 9). The number of recombinants is lower than can be inferred from the genetic distance and consistent with suppressed recombination, which was expected because of the inter-specific origins of the introgressions.

Example 6

Recombinants Carrying the Tm2a and SP_Lin5 Loci in Coupling Phase

The 8 putative recombinants obtained in Example 5 were self pollinated and 96 individuals of each family screened with markers linked to Lin5 and ToMV resistance. A total of 99 recombinants homozygous for Tm2a and SP_Lin5 were identified among the progeny. The distribution of genotypic classes of families exclusively segregating for SP_Lin5 was found to be non-Mendelian ($p<0.001$) and biased towards individuals only carrying Tm2a homozygously. The suppressed recombination and skewed segregation demonstrate the difficulty in obtaining the desired recombinant. However, the described markers and introgression fragments allowed the event to be reproduced in open field, resulting in round tomatoes and pear-shaped processing types.

TABLE 9

Disease scores of recombinant 13KI1000 screened with FCRR (FOR) and ToMV. Disease symptoms were scored on individual seedlings on a 1-9 scale. Disease index score 1 indicates total absence of symptoms, score 9 is highly symptomatic (ToMV) or dead plant (FOR).

| Line | Plant# | Score | Pathogen | Line | Plant# | Score | Pathogen |
|---|---|---|---|---|---|---|---|
| Control | 1 | 9 | ToMV | Control | 1 | 9 | FOR |
| Control | 2 | 9 | ToMV | Control | 2 | 9 | FOR |
| Control | 3 | 9 | ToMV | Control | 3 | 9 | FOR |
| 13KI1000 | 1 | 1 | ToMV | 13KI1000 | 1 | 1 | FOR |
| 13KI1000 | 2 | 1 | ToMV | 13KI1000 | 2 | 1 | FOR |
| 13KI1000 | 3 | 1 | ToMV | 13KI1000 | 3 | 1 | FOR |
| 13KI1000 | 4 | 1 | ToMV | 13KI1000 | 4 | 1 | FOR |
| 13KI1000 | 5 | 1 | ToMV | 13KI1000 | 5 | 1 | FOR |
| 13KI1000 | 6 | 1 | ToMV | 13KI1000 | 6 | 1 | FOR |
| 13KI1000 | 7 | 1 | ToMV | 13KI1000 | 7 | 1 | FOR |
| 13KI1000 | 8 | 1 | ToMV | 13KI1000 | 8 | 1 | FOR |
| 13KI1000 | 9 | 1 | ToMV | 13KI1000 | 9 | 1 | FOR |
| 13KI1000 | 10 | 1 | ToMV | 13KI1000 | 10 | 1 | FOR |
| 13KI1000 | 11 | 1 | ToMV | 13KI1000 | 11 | 1 | FOR |
| 13KI1000 | 12 | 1 | ToMV | 13KI1000 | 12 | 1 | FOR |
| 13KI1000 | 13 | 1 | ToMV | | | | |
| 13KI1000 | 14 | 1 | ToMV | | | | |
| 13KI1000 | 15 | 1 | ToMV | | | | |
| 13KI1000 | 16 | 1 | ToMV | | | | |
| 13KI1000 | 17 | 1 | ToMV | | | | |
| 13KI1000 | 18 | 1 | ToMV | | | | |
| 13KI1000 | 19 | 1 | ToMV | | | | |

Table 10 shows Brix measurements for 2-3 fruits of 4-8 plants of two original and corresponding converted parental lines comprising the SP_Lin5/Fr1/Tm2a event. The data are consistent with a Brix increase upon introduction of the coupling event in inbred lines of multiple backgrounds.

TABLE 10

Brix measurements for 2-3 fruits of 4-8 plants of two original and corresponding converted parental lines. The data are consistent with a Brix increase upon introduction of the coupling event in inbred lines of multiple backgrounds.

| Type | Background | Plot number | plant # | Brix FRUIT#1 | Brix FRUIT#2 | Brix FRUIT#3 | Avg. BX per plant | | Mean | STD |
|---|---|---|---|---|---|---|---|---|---|---|
| Mini-Plum | Line A | 15 | 1 | 7.3 | 6.7 | | 7.00 | | | |
| | Line A | 15 | 2 | 9.7 | 10.1 | | 9.90 | Line A | 8.908 | 1.142110619 |
| | Line A | 15 | 3 | 10.1 | 9.9 | | 10.00 | Line A + SP_Lin5 + Fr + Tm | 9.54 | 1.054575568 |
| | Line A | 15 | 4 | 9.7 | 9 | | 9.35 | Line B | 10 | 0.529445465 |
| | Line A | 15 | 5 | 8.4 | 9.6 | | 9.00 | Line B + SP_Lin5 + Fr + Tm | 10.81 | 0.799305254 |
| | Line A | 15 | 6 | 8.2 | 8.2 | | 8.20 | | | |
| | BC2F9[A + SP_Lin5 + Fr + Tm] | 69 | 1 | 10.9 | 10.4 | 11.3 | 10.87 | | | |
| | BC2F9[A + SP_Lin5 + Fr + Tm] | 69 | 2 | 9.5 | 9.5 | 9.9 | 9.63 | | | |
| | BC2F9[A + SP_Lin5 + Fr + Tm] | 69 | 3 | 10.1 | 8.9 | 9.1 | 9.37 | | | |
| | BC2F9[A + SP_Lin5 + Fr + Tm] | 69 | 4 | 8.5 | 8.3 | 8.1 | 8.30 | | | |
| Round Cherry | Line B | 664 | 1 | 9.8 | 10.2 | | 10.00 | | | |
| | Line B | 664 | 2 | 10 | 9.7 | | 9.85 | | | |
| | Line B | 664 | 3 | 10.8 | 10.5 | | 10.65 | | | |
| | Line B | 664 | 4 | 10.7 | 9.7 | | 10.20 | | | |
| | Line B | 664 | 5 | 9.9 | 11.5 | | 10.70 | | | |
| | Line B | 664 | 6 | 8.3 | 11.4 | | 9.85 | | | |
| | Line B | 664 | 7 | 8.6 | 9.5 | | 9.05 | | | |
| | Line B | 664 | 8 | 10.4 | 9.1 | | 9.75 | | | |
| | BC4F7[B + SP_Lin5 + Fr + Tm] | 672 | 1 | 10.7 | 11.1 | 10.2 | 10.67 | | | |
| | BC4F7[B + SP_Lin5 + Fr + Tm] | 672 | 2 | 10.3 | 12.8 | 12 | 11.70 | | | |
| | BC4F7[B + SP_Lin5 + Fr + Tm] | 672 | 3 | 10 | 10.1 | 9.3 | 9.80 | | | |
| | BC4F7[B + SP_Lin5 + Fr + Tm] | 672 | 4 | 10.6 | 10.7 | 12 | 11.10 | | | |

Example 7

Heterozygous Deployment of Pen1/SP_Lin5

Pen1 (Alseekh et al., *Trends Plant Sci* 18(10):536-8) is a distinct Brix allele that, when combined with SP_Lin5, confers a significant and perceptible Brix increase. Pen1 can be introgressed from commercial processing varieties, including types AB-2, DRI-0311, and JAG-8810 using trait linked marker NSLYC005704029 (SEQ ID NO:23) and primers/probes listed in Table 11. Candidate genes within the Pen1 introgression are described by Causse et al., 2004 and Baxter et al., 2005.

TABLE 11

SEQ ID NOs for NSLYC005704029 marker assay.

| Marker Name | Forward Primer Sequence | Reverse Primer Sequence | Probe 1 Sequence | Probe 2 Sequence |
|---|---|---|---|---|
| NSLYC005704029 | 24 | 25 | 26 | 27 |

Figure 7:
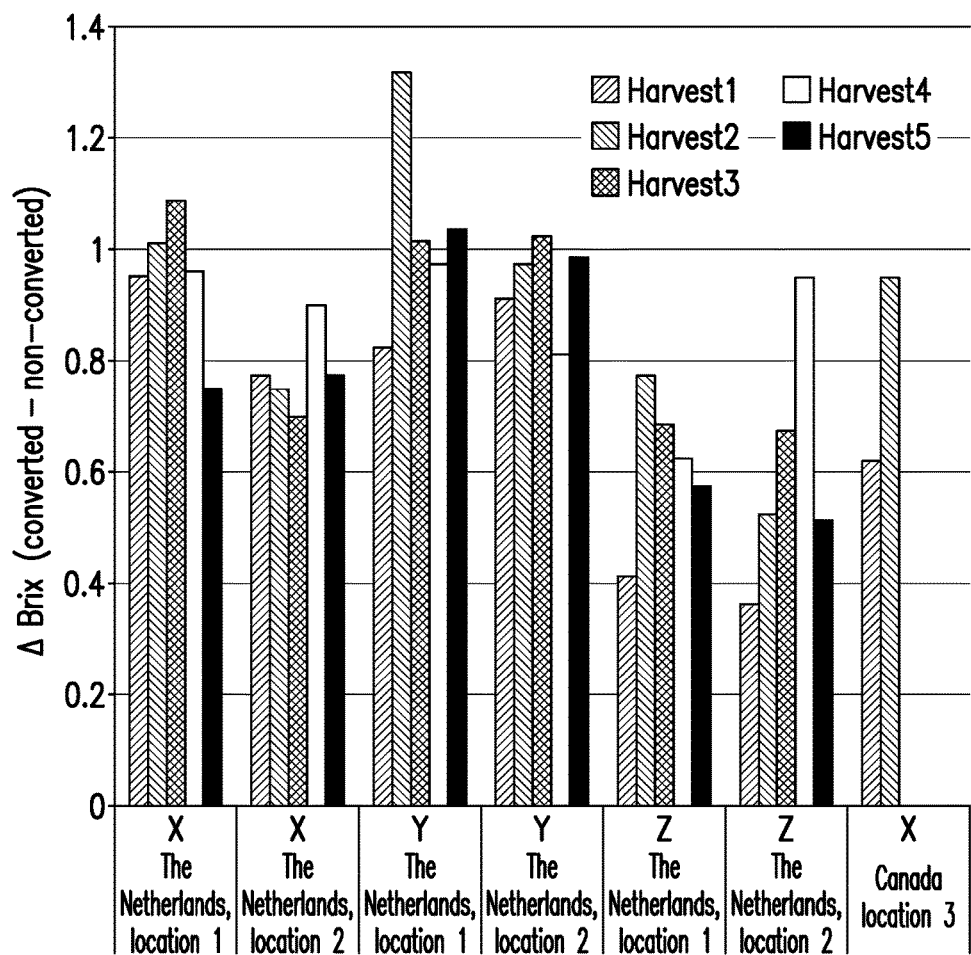
FIG. 7: Shows Brix increase observed for the hybrids Hybrid X, Hybrid Y, and Hybrid Z carrying both Pen1 and SP_Lin5 in the heterozygous phase. Five versions of converted hybrids were tested in at least two locations and compared to the original commercial varieties. The data are consistent with a Brix increase for all conversions. An increase of 1 degree Brix was observed in two locations.

FIG. 7 shows the Brix increase observed for hybrids Hybrid X, Hybrid Y, and Hybrid Z which carry both Pen1 and SP_Lin5 in the heterozygous phase. During the experiment five Brix measurements were done. Hybrids were tested in at least two locations and compared to the original commercial varieties. The data are consistent with a Brix increase for all conversions. An increase of 1 degree Brix was observed in two locations.

Example 8

Pen1/Fr1/SP_Lin5/Tm2a Event

Plants comprising a combined Pen1/Fr1/SP_Lin5/Tm2a introgression were developed using the combined Fr1/SP_Lin5/Tm2a introgression of the present invention together with a Pen1 introgression. Plants comprising a Pen1/Fr1/SP_Lin5/Tm2a introgression are selected during breeding using one or more markers within the Fr1/SP_Lin5/Tm2a introgression of the present invention, for example markers NSLYC008433807, NSLYC008433769, NSLYC009194570, NL0217199, or NSLYC009229170, together with markers for Pen1, for example markers within regions described by Alseekh et al., *Trends Plant Sci* 18(10): 536-8 or trait linked marker NSLYC005704029. Markers for detecting Pen1 introgressions are publically available and can be retrieved from the Sol Genomics Network (solgenomics.net). Pen 1 introgressions can be obtained from the commercial processing varieties such as AB-2, DRI-0311 and JAG-8810.

Plants comprising the Pen1/Fr1/SP_Lin5/Tm2a introgression exhibit a significant and perceptible increase in Brix compared with plants lacking the introgression.

Example 9

Tm1/Fr1/SP_Lin5/Tm2a Event

Plants comprising a combined Tm1/Fr1/SP_Lin5/Tm2a introgression are produced using the combined Fr1/SP_Lin5/Tm2a introgression of the present invention together with a Tm1 introgression. Plants comprising a Tm1/Fr1/SP_Lin5/Tm2a introgression are selected during breeding using one or more markers within the Fr1/SP_Lin5/Tm2a introgression of the present invention, for example markers NSLYC008433807, NSLYC008433769, NSLYC009194570, NL0217199, or NSLYC009229170, together with markers for Tm1, for example markers within regions described by Arens, et al., *Theor Appl Genet* (2010) 120:655-664. Markers for detecting Tm1 introgressions are publically available and can be detected by assays using publically available sequences, for example assays using primers SCN20F and SCN20R described in Arens, et al. 2010. Tm1 introgressions can be obtained from the commercial processing varieties such as Master no 2 and NAK 83.

Plants comprising the Tm1/Fr1/SP_Lin5/Tm2a introgression exhibit resistance to a distinct subset of ToMV isolates with reduced necrosis compared with plants lacking the introgression.

Example 10

Stacking of Pen1 and SP_Lin5 Loci with Additive Effect

In order to test the Brix effect of a stack of Pen1 and SP_Lin5 alleles in an elite background, a BC4F2 family was developed using the Komeett hybrid as the female parent. The BC4F2 family contained all 9 possible genetic combinations of Pen1 and SP_Lin5 (Table 12) and were preselected from the population using the herein described trait-linked markers. Similar genotypes were planted together in a plot. The resulting crosses were subsequently tested for Brix.

TABLE 12

Genetic combinations of the BC4F2 family tested for Brix. Pen9 refers to the shortened SP_Lin5 introgression from *S. pennellii*.

| Entry | Pen1 | Pen1 | Description |
|---|---|---|---|
| 1 | +/+ | +/+ | null |
| 2 | +/+ | Pen9/+ | |
| 3 | +/+ | Pen9/Pen9 | |
| 4 | Pen1/+ | +/+ | |
| 5 | Pen1/+ | Pen9/+ | het double stack |
| 6 | Pen1/+ | Pen9/Pen9 | |
| 7 | Pen1/Pen1 | +/+ | |
| 8 | Pen1/Pen1 | Pen9/+ | |
| 9 | Pen1/Pen1 | Pen9/Pen9 | horn double stack |

Brix was evaluated for two harvests. Two have representative fruit, only the upper 2-3 fruits of a cluster were included for sampling, from all four plants in a plot. For data analysis, the average Brix % per plot was calculated and used in an ANOVA where genotype was the fixed factor and Brix % the variable. From the Brix % the ΔBrix was calculated by taking the difference between the genotype of interest and the homozygous wild type (control). A post-hoc test was performed on the Brix % data in order to distinguish effects between genotypes. The analysis was performed in JMP® software (SAS, Carey, N.C.).

Figure 8:
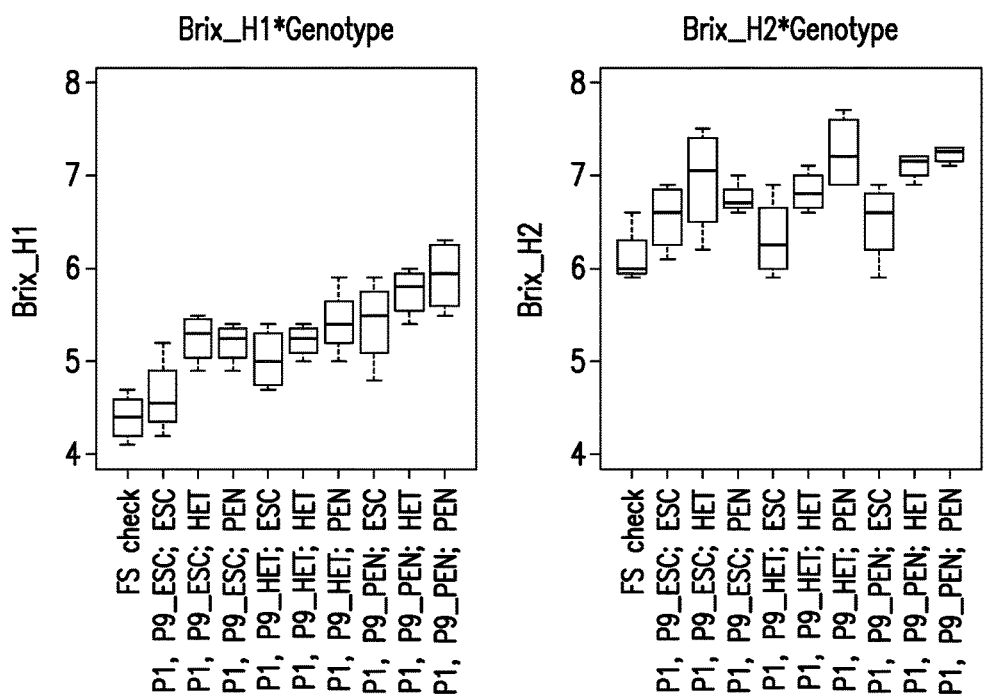
FIG. 8: Shows raw data boxplots for Brix from harvest 1 (BrixH1) and harvest 2 (BrixH2). Genotypes described on the x-axis show the consecutive status of Pen1 (P1) locus followed by the status of SP_Lin5 locus (P9). Esc=homozygote wild type; Het=heterozygous; Pen=homozygote for the Brix increasing locus from *S. pennellii*.

Raw data from harvest 1 and harvest 2 is plotted in FIG. 8. As shown in the figure, the mean Brix values across genotypes of harvest 2 are >1% higher than harvest 1. This may result from the increased light intensity and/or longer day length the higher clusters in the plant were exposed to. It is notable that the differences in Brix increase caused by the Pen1/SP_Lin5 alleles are larger in the first harvest. Here also a more or less steady Brix increase is observed with increased presence of Pen alleles (No Pen alleles<Heterozygous Pen alleles<Homozygous Pen alleles). In the second harvest heterozygous and homozygous double stacks confer an equally high Brix increase.

For the first harvest a significant increase in Brix is observed when a single heterozygous allele of Pen1 or SP_Lin5 is present (Table 13). However, this was not observed in harvest 2. In harvest 1, the highest Brix increase was obtained with a homozygous double stack and a double stack with Pen1 fixed and SP_Lin5 heterozygous (Table 13). For the harvest 2, all homozygous and heterozygous double stacks show an similar significant Brix increase with both heterozygous and homozygous single SP_Lin5 belonging to the same group (Table 13). It was also observed that the Brix increase from homozygous single stacks adds up to the same Brix increase of the homozygous double stack in the first harvest. In harvest 2, the Brix increase of the homozygous double stack is much higher than the combined values of the homozygous single stacks.

TABLE 13

Average Brix measurements for the different genotypes separated in groups according to the post hoc test on Brix %. Genotypes show first the status of the Pen1 locus (P1) and then the status of SP_Lin5 locus (P9).

| Genotype | Harvest 1 | | | Harvest 2 | | |
|---|---|---|---|---|---|---|
| | Group | BRIX % | ΔBRIX | Group | BRIX % | ΔBRIX |
| P1, P9_ESC_ESC | D E | 4.63 | | D | 6.55 | |
| P1, P9_ESC_HET | C | 5.25 | 0.62 | B C D | 6.95 | 0.40 |
| P1, P9_ESC_PEN | C | 5.20 | 0.57 | A B | 6.75 | 0.20 |
| P1, P9_HET_ESC | C D | 5.03 | 0.40 | C D | 6.33 | -0.22 |
| P1, P9_HET_HET | C | 5.23 | 0.60 | A B C | 6.83 | 0.28 |
| P1, P9_HET_PEN | B C | 5.43 | 0.80 | A | 7.25 | 0.70 |

TABLE 13-continued

Average Brix measurements for the different genotypes separated in groups according to the post hoc test on Brix %. Genotypes show first the status of the Pen1 locus (P1) and then the status of SP_Lin5 locus (P9).

| Genotype | Harvest 1 | | | | Harvest 2 | | | | |
|---|---|---|---|---|---|---|---|---|---|
| | Group | | BRIX % | ΔBRIX | Group | | | BRIX % | ΔBRIX |
| P1, P9_PEN_ESC | B | C | 5.43 | 0.80 | B | C | D | 6.50 | −0.05 |
| P1, P9_PEN_HET | A | B | 5.75 | 1.12 | A | | | 7.10 | 0.55 |
| P1, P9_PEN_PEN | A | | 5.93 | 1.30 | A | | | 7.23 | 0.68 |

Esc = homozygote wild type;
Het = heterozygous;
Pen = homozygote for the Brix increasing locus from *S. pennellii*.
ΔBrix is calculated as the difference in Brix between the genotype of interest and the homozygous wild type.

This data shows that homozygous double stack provide the largest Brix increase. This Brix increase is surprisingly not inhibited by negative epistasis, as suggested by Eshed & Zamir (1996). In fact, in the second harvest a positive epistatic effect was observed. However, as the season progresses the increase in Brix is smaller. Fruit clusters formed in early spring season show a maximum increase of Δ 1.3, while fruit clusters formed towards the summer show a maximum increase of Δ 0.7. This could be the result of a higher light intensity in the greenhouse during the summer period. Nevertheless, overall Brix values are higher in summer than in spring.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A *Solanum lycopersicum* plant, the plant comprising a Lin5 allele from *Solanum pennellii* and a Pen1 allele from *Solanum pennellii*, wherein the Lin5 allele further comprises marker NSLYC009194570, marker NL0217199, or marker NSLYC009229170 and the Pen1 allele further comprises marker NSLYC005704029, and wherein the plant exhibits elevated Brix levels relative to a plant lacking the Lin5 and Pen1 alleles.

2. The plant of claim 1, wherein the Brix levels of the plant are equal to or greater than the levels of a plant comprising only the Lin5 allele added to the levels of a plant comprising only the Pen1 allele.

3. The plant of claim 1, wherein the plant is homozygous for said Lin5 allele.

4. The plant of claim 1, wherein the plant is heterozygous for said Lin5 allele.

5. The plant of claim 1, wherein the plant is homozygous for said Pen1 allele.

6. The plant of claim 1, wherein the plant is heterozygous for said Pen1 allele.

7. The plant of claim 1, further comprising a Fr1 allele from *Solanum peruvianum*, and a Tm2a allele from *Solanum peruvianum*, wherein the Fr1 allele further comprises marker NSLYC008433807 or marker NSLYC008433769, and wherein said plant exhibits improved resistance to *Fusarium* crown and root rot and tomato mosaic virus relative to a plant lacking the Fr1 allele from *Solanum peruvianum*, and a Tm2a allele from *Solanum peruvianum*.

8. The plant of claim 7, wherein the plant is homozygous for said Fr1 allele from *Solanum peruvianum*.

9. The plant of claim 7, wherein the plant is homozygous for said Tm2a allele from *Solanum peruvianum*.

10. The plant of claim 9, wherein the plant exhibits decreased necrosis compared with a plant that is heterozygous for said Tm2a allele from *Solanum peruvianum*.

11. The plant of claim 1, wherein the plant is inbred.

12. The plant of claim 1, wherein the plant is hybrid.

13. A plant part of the plant of claim 1, wherein the plant part comprises a cell of said plant.

14. The plant part of claim 13, wherein the plant part is a leaf, root, flower, fruit, pollen, ovule, or part thereof.

15. A seed that produces the plant of claim 1.

16. The plant of claim 7, comprising said Pen1 allele and comprising a recombined chromosomal segment comprising said Lin5 allele, said Fr1 allele, and said Tm2a allele, which confers improved resistance to *Fusarium* crown and root rot and tomato mosaic virus, and elevated Brix levels relative to a plant lacking said segment.

17. A plant part of the plant of claim 16, wherein the plant part comprises a cell of said plant.

18. The plant part of claim 17, wherein the plant part is a leaf, root, flower, fruit, pollen ovule, seed, or part thereof.

19. A seed that produces the plant of claim 16.

20. A *Solanum lycopersicum* plant comprising a recombined chromosomal segment comprising a Fr1 allele from *Solanum peruvianum*, a Tm2a allele from *Solanum peruvianum*, and a Lin5 allele from *Solanum pennellii*, wherein the Fr1 allele further comprises marker NSLYC008433807 or marker NSLYC008433769, wherein the Lin5 allele further comprises marker NSLYC009194570, marker NL0217199, or marker NSLYC009229170, and wherein a representative sample of seed comprising said chromosomal segment was deposited under ATCC Accession Number PTA-121480.

21. The plant of claim 1, comprising a *Solanum pennellii* allele at marker NSLYC005704029, and a *Solanum pennellii* allele at marker NSLYC009229170, wherein the fruit of said plant exhibits elevated Brix levels relative to the fruit of a plant lacking the Lin5 and Pen1 alleles.

22. A method for producing a hybrid *Solanum lycopersicum* plant with elevated Brix levels, comprising crossing the plant of claim 1 with a second *Solanum lycopersicum* plant of a different genotype and selecting for a hybrid *Solanum lycopersicum* plant with elevated Brix levels relative to a plant lacking the Lin5 and Pen1 alleles.

23. A method for producing a plurality of hybrid *Solanum lycopersicum* plants with elevated Brix levels, comprising crossing the plant of claim 1 with a plurality of second *Solanum lycopersicum* plants of different genotypes and selecting for hybrid *Solanum lycopersicum* plants with elevated Brix levels relative to plants lacking the Lin5 and Pen1 alleles.

* * * * *

```
                        SEQUENCE LISTING

<160> NUMBER OF SEQ ID NOS: 30

<210> SEQ ID NO 1
<211> LENGTH: 33
<212> TYPE: DNA
<213> ORGANISM: Artificial sequence
<220> FEATURE:
<223> OTHER INFORMATION: Primer

<400> SEQUENCE: 1
gattaagggt gttgaatatg aatttgttga aga                              33

<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
gccattgtga attagcactg gaat                                        24

<210> SEQ ID NO 3
<211> LENGTH: 24
<212> TYPE: DNA
<213> ORGANISM: Artificial sequence
<220> FEATURE:
<223> OTHER INFORMATION: Probe

<400> SEQUENCE: 3
atttacataa caaaagtcct ctac                                        24
```

```
<210> SEQ ID NO 4
<211> LENGTH: 24
<212> TYPE: DNA
<213> ORGANISM: Artificial sequence
<220> FEATURE:
<223> OTHER INFORMATION: Probe

<400> SEQUENCE: 4
atttacataa caaaagtcct gtac                                              24

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
catctcacaa gcttcctctt tacct                                             25

<210> SEQ ID NO 6
<211> LENGTH: 25
<212> TYPE: DNA
<213> ORGANISM: Artificial sequence
<220> FEATURE:
<223> OTHER INFORMATION: Primer

<400> SEQUENCE: 6
gcggtggtaa gtactttcat acgta                                             25

<210> SEQ ID NO 7
<211> LENGTH: 19
<212> TYPE: DNA
<213> ORGANISM: Artificial sequence
<220> FEATURE:
<223> OTHER INFORMATION: Probe

<400> SEQUENCE: 7
aaggagagga acgagagaa                                                    19

<210> SEQ ID NO 8
<211> LENGTH: 19
<212> TYPE: DNA
<213> ORGANISM: Artificial sequence
<220> FEATURE:
<223> OTHER INFORMATION: Probe

<400> SEQUENCE: 8
aaggagagga acaagagaa                                                    19

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
gaagggattg agaatcgact atggt                                             25

<210> SEQ ID NO 10
<211> LENGTH: 24
<212> TYPE: DNA
<213> ORGANISM: Artificial sequence
<220> FEATURE:
<223> OTHER INFORMATION: Primer
```

<400> SEQUENCE: 10
cccttcgatt tctgctagga tcat                                      24

<210> SEQ ID NO 11
<211> LENGTH: 20
<212> TYPE: DNA
<213> ORGANISM: Artificial sequence
<220> FEATURE:
<223> OTHER INFORMATION: Probe

<400> SEQUENCE: 11
atttctatgc atcgaagaca                                           20

<210> SEQ ID NO 12
<211> LENGTH: 17
<212> TYPE: DNA
<213> ORGANISM: Artificial sequence
<220> FEATURE:
<223> OTHER INFORMATION: Probe

<400> SEQUENCE: 12
tctatgcatc aaagaca                                              17

<210> SEQ ID NO 13
<211> LENGTH: 27
<212> TYPE: DNA
<213> ORGANISM: Artificial sequence
<220> FEATURE:
<223> OTHER INFORMATION: Primer

<400> SEQUENCE: 13
cattcagtat tcttctcttg cctgtct                                   27

<210> SEQ ID NO 14
<211> LENGTH: 25
<212> TYPE: DNA
<213> ORGANISM: Artificial sequence
<220> FEATURE:
<223> OTHER INFORMATION: Primer

<400> SEQUENCE: 14
aggagttcca atgctcattt tcagt                                     25

<210> SEQ ID NO 15
<211> LENGTH: 24
<212> TYPE: DNA
<213> ORGANISM: Artificial sequence
<220> FEATURE:
<223> OTHER INFORMATION: Probe

<400> SEQUENCE: 15
tgactaaatt ttaccagtac aaac                                      24

<210> SEQ ID NO 16
<211> LENGTH: 22
<212> TYPE: DNA
<213> ORGANISM: Artificial sequence
<220> FEATURE:
<223> OTHER INFORMATION: Probe

<400> SEQUENCE: 16
actaaatttt accaatacaa ac                                        22

<210> SEQ ID NO 17
<211> LENGTH: 27
<212> TYPE: DNA
<213> ORGANISM: Artificial sequence
<220> FEATURE:
<223> OTHER INFORMATION: Primer

<400> SEQUENCE: 17
tccagctaga gaggataaac tgagtac                               27

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
gctggaaaga ctaccaagtt gctt                                  24

<210> SEQ ID NO 19
<211> LENGTH: 16
<212> TYPE: DNA
<213> ORGANISM: Artificial sequence
<220> FEATURE:
<223> OTHER INFORMATION: Probe

<400> SEQUENCE: 19
cactgaccga ttatca                                           16

<210> SEQ ID NO 20
<211> LENGTH: 16
<212> TYPE: DNA
<213> ORGANISM: Artificial sequence
<220> FEATURE:
<223> OTHER INFORMATION: Probe

<400> SEQUENCE: 20
cactgaccgg ttatca                                           16

<210> SEQ ID NO 21
<211> LENGTH: 24
<212> TYPE: DNA
<213> ORGANISM: Artificial sequence
<220> FEATURE:
<223> OTHER INFORMATION: Primer

<400> SEQUENCE: 21
ggtgctccgt cgatgcaaag tgca                                  24

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
ggtgctccgt agacataaaa tcta                                  24

<210> SEQ ID NO 23
<211> LENGTH: 576
<212> TYPE: DNA
<213> ORGANISM: Artificial sequence
<220> FEATURE:
<223> OTHER INFORMATION: Marker

```
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t

<400> SEQUENCE: 23
ggacatgggg ctaagctcta tgataatact gccatggana atttacttaa aagtntcgaa      60
attataagga gattcagggc agcgcagttt gatctagtta aggcaggaca gaaagctgaa     120
ggcgaagtca tttctgttaa tatggtcttc ttgaaagctg gcacccctc acctctgta      180 agtcagtcta gctatttgac tctgaccact gcttcctgca tattgtgacc attttcttc    240 tgaggaattc taggagtctt tgattgagct tattcatcca atgtgctggg ttntaacctt   300
aaacactatt tgatagtgtt taccanttat tcagattnga gtttaaatgt ttgaagagct   360
taaatgtttc agaattatta atgtagtcaa gtgaaaacga atatttgaag tgatggcgta   420
gcagatatag ggtgttttac cgaacaatcc tttcttgtaa aacaatggcc cgtttcccta   480
cacttagaat cagaattgag ataaagtttta aaacatggac ttctttattt ctgtggcagg  540
gttttgtcat gaacctgcag ccatctgaag cccaag                             576

<210> SEQ ID NO 24
<211> LENGTH: 25
<212> TYPE: DNA
<213> ORGANISM: Artificial sequence
<220> FEATURE:
<223> OTHER INFORMATION: Primer

<400> SEQUENCE: 24
gcttcctgca tattgtgacc atttt                                           25

<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25
cccagcacat tggatgaata agc                                             23

<210> SEQ ID NO 26
<211> LENGTH: 18
<212> TYPE: DNA
<213> ORGANISM: Artificial sequence
<220> FEATURE:
<223> OTHER INFORMATION: Probe

<400> SEQUENCE: 26
aagactccta gaattcct                                                   18
```

```
<210> SEQ ID NO 27
<211> LENGTH: 17
<212> TYPE: DNA
<213> ORGANISM: Artificial sequence
<220> FEATURE:
<223> OTHER INFORMATION: Probe

<400> SEQUENCE: 27
aagactccta gattcct                                                        17

<210> SEQ ID NO 28
<211> LENGTH: 89
<212> TYPE: DNA
<213> ORGANISM: Tomato

<400> SEQUENCE: 28
tttggggttg gtcaaatgaa tcggatgtat tacctgacga tgatattaag aaaggatggg         60
ctggaattca aggtattccg cgacaagta                                           89

<210> SEQ ID NO 29
<211> LENGTH: 89
<212> TYPE: DNA
<213> ORGANISM: Tomato

<400> SEQUENCE: 29
tttggggttg gtcaaatgaa tccgatgtat tacctgacga tgaaattaag aaaggatggg         60
ctggaattca aggtattccg cgacaagta                                           89

<210> SEQ ID NO 30
<211> LENGTH: 74
<212> TYPE: DNA
<213> ORGANISM: Tomato

<400> SEQUENCE: 30
tttggggttg gtcaaatgaa tcggatgaaa ttaagaaagg atgggctgga attcaaggta         60
ttccgcgaca agta                                                           74
```